(12) United States Patent
Botta et al.

(10) Patent No.: US 11,104,657 B2
(45) Date of Patent: Aug. 31, 2021

(54) NOTCH INHIBITORS FOR USE IN THE TREATMENT OF T-CELL ACUTE LYMPHOBLASTIC LEUKEMIA

(71) Applicants: UNIVERSITÀ DEGLI STUDI DI ROMA "LA SAPIENZA", Rome (IT); FONDAZIONE ISTITUTO ITALIANO DI TECNOLOGIA, Genoa (IT)

(72) Inventors: Bruno Botta, Manziana (IT); Isabella Screpanti, Rome (IT); Luca Tottone, La Maddalena (IT); Nadezda Zhdanoskaya, Rome (IT); Cinzia Ingallina, Latina (IT); Francesca Giulimondi, Rome (IT); Deborah Quaglio, Santa Marinella (IT); Rocco Palermo, Rome (IT); Mattia Mori, Castelnuovo Berardegna (IT); Francesca Ghirga, Civitavecchia (IT)

(73) Assignees: FONDAZIONE ISTITUTO ITALIANO DI TECNOLOGIA, Genoa (IT); UNIVERSITÀ DEGLI STUDI DI ROMA "LA SAPIENZA", Rome (IT)

( * ) Notice: Subject to any disclaimer, the term of this patent is extended or adjusted under 35 U.S.C. 154(b) by 0 days.

(21) Appl. No.: 16/473,986

(22) PCT Filed: Dec. 20, 2017

(86) PCT No.: PCT/IB2017/058204
§ 371 (c)(1),
(2) Date: Jun. 26, 2019

(87) PCT Pub. No.: WO2018/122689
PCT Pub. Date: Jul. 5, 2018

(65) Prior Publication Data
US 2019/0337916 A1 Nov. 7, 2019

(30) Foreign Application Priority Data
Dec. 29, 2016 (IT) .................. 102016000132360

(51) Int. Cl.
| | |
|---|---|
| *C07D 309/32* | (2006.01) |
| *C07D 309/12* | (2006.01) |
| *A61P 35/02* | (2006.01) |
| *C07C 49/248* | (2006.01) |
| *C07C 49/835* | (2006.01) |
| *C07C 49/84* | (2006.01) |
| *A61K 31/121* | (2006.01) |

(52) U.S. Cl.
CPC ............ *C07D 309/32* (2013.01); *A61P 35/02* (2018.01); *C07C 49/248* (2013.01)

(58) Field of Classification Search
CPC ..... C07D 309/32; C07D 309/12; A61P 35/02; C07C 49/248; C07C 49/835; C07C 49/84; A61K 31/121
See application file for complete search history.

(56) References Cited

U.S. PATENT DOCUMENTS

| | | |
|---|---|---|
| 2002/0040029 A1 | 4/2002 | Bowen |
| 2015/0175548 A1 | 6/2015 | Kaether |

FOREIGN PATENT DOCUMENTS

| | | | |
|---|---|---|---|
| CN | 1990446 A | * | 7/2007 |
| EP | 2606884 A1 | | 6/2013 |

OTHER PUBLICATIONS

Abdelwahab, S. I., "Zerumbone induces apoptosis in T-acute lymphoblastic leukemia cells." Leukemia Research 35.2 (2011): 268-271.*
Roti et al., Complementary Genomic Screens Identify Serca as a Therapeutic Target in NOTCH1 Mutated Cancer, Cancer Cell, 23:390-405 (2013).
Youns et al., Sensitivity and resistence towards isoliquiritigenin, doxorubicin and methotrexate in T cell acute lymphoblastic leukaemia cell lines by pharmacogenomics, Naunyn-Schmied Arch Pharmacol, 382:221-234 (2010).
Mai et al., Chalcones with electron-withdrawing and electron-donating substituents: Anticancer activity against TRAIL resistant cancer cells, structure—activity relationship analysis and regulation of apoptotic proteins, European Journal of Medicinal Chemistry, 77:378-387 (2014).
Kupcewicz et al., Cytotoxic activity of substituted chalcones in terms of molecular electronic properties, Bioor. Med. Chem. Lett. 24:4260-4265 (2014).

(Continued)

*Primary Examiner* — John M Mauro
(74) *Attorney, Agent, or Firm* — Nevrivy Patent Law Group P.L.L.C.

(57) ABSTRACT

Compounds of formula (I) in the capacity of compounds with anti-tumor activity for the treatment of T-cell acute lymphoblastic leukemia (T-ALL).

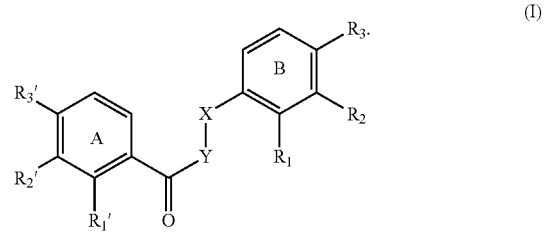

(I)

3 Claims, 4 Drawing Sheets

(56) References Cited

OTHER PUBLICATIONS

Boumendjel et al., Antimitotic and Antiproliferative Activities of chalcones: Forward Structure-Activity Relationship, J. Med. Chem. 51:2307-2310 (2008).
Tanaka et al., Influence of Natural and Synthetic compounds on Cell Surface Expression of Cell Adhesion Molecules, ICAM-1 and VCAM-1, Planta Med 67:108-113 (2001).
Pardede et al., Flavonoid profile and antileukemic activity of Coreopsis lanceolata flowers, Bioorg. Med. Chem. Lett., 26:2784-2787 (Apr. 2016).
Ducki et al., Combretastatin-like chalcones as inhibitors of microtubule polymerizaton. Part 1: Synthesis and biological evaluation of antivascular activity, Bioorganic & Medicinal Chemistry, 17:7698-7710 (2009).
Mori et al., Identification of a novel chalcone derivative that inhibits Notch signaling in T-cell acute lymphoblastic leukemia, Scientific Reports, 7:1-13 (2017).
International Search Report from Int. Appl. No. PCT/IB2017/058204, dated Mar. 14, 2018.
Kunnimalaiyaan et al., Xanthohumol inhibits Notch signaling and induces apoptosis in hepatocellular carcinoma. PloSone, (2015), 10:1-12, e0127464.

\* cited by examiner

Fig. 1

Claisen-Schmidt reaction

Deprotection

NOTCH INHIBITORS FOR USE IN THE TREATMENT OF T-CELL ACUTE LYMPHOBLASTIC LEUKEMIA

FIELD OF THE INVENTION

The present description relates to new Notch inhibitor compounds for use in the treatment of T-cell acute lymphoblastic leukemia.

BACKGROUND OF THE INVENTION

Notch signaling is an inter-cellular communication system that plays a key role in regulating biological processes of primary importance, such as self-maintenance and stem cell differentiation in embryonic development and in homeostasis in different tissues of the adult organism.

In mammals, the Notch family comprises four transmembrane receptors (Notch1-4), highly conserved from an evolutionary point of view, and five ligands (Jagged-1, -2, Delta-like-1, -3 and -4).

Notch signaling activation occurs through the interaction of the extracellular domain of a Notch receptor, expressed on the membrane of a cell receiving the signal, with a ligand present on the membrane of a signaling cell. Interaction with the ligand predisposes the Notch receptor to two consecutive proteolytic cuts, by the enzymatic action of the TACE complex (ADAM metalloprotease TNF-α converting enzyme) before, and of the gamma-secretase complex after, which culminate with the release of the active Notch intracellular domain (NICD), which moves into the nucleus and promotes the expression of specific target genes.

The constitutive activation of the pathway, due to mutations, gene amplifications or post-translational changes to Notch receptors, is directly related to the development, progression, angiogenesis, and poor prognosis in a large number of oncologic pathologies, including T-cell acute lymphoblastic leukemia (T-ALL).

Therefore, one of the objectives of the research, aimed at developing innovative therapies for curing T-ALL, is the pharmacological inhibition of Notch signaling.

In this context, to date, the most promising approach and the examination of several clinical trials involves blocking the proteolytic cut of the Notch receptor that leads to the release of the activated domain through treatment with small molecules of gamma-secretase inhibitors (GSIs). Unfortunately, as revealed by clinical studies, potential clinical applications of GSIs in anti-tumor therapies are limited by primary resistance and/or side effects associated with the treatments. In particular, it has been shown that exposure to GSIs often accompanies the onset of metaplasia of the goblet cells of the intestine.

A second strategy, alternative to the use of GSIs, involves the use of selectively directed monoclonal antibodies against Notch receptors and/or ligands, but this approach also has intrinsic limits. The efficacy of the action of ligand-competitive antibodies is closely related to the expression levels of the receptors and their ligands, and the different affinity of the four Notch receptors for the respective ligands. Furthermore, the therapeutic use of antibodies may be ineffective in T-ALL subgroups in which the signaling is constitutively activated due to chromosomal translocations or Notch gene mutations.

Given the high number of diseases and tumors associated with the deregulation of the Notch pathway, it is even more necessary to develop new, efficient, specific and safe therapies directed at the inhibition of this signaling in order to effectively counteract resistance, recurrence and metastatization phenomena in different solid and hematologic tumors including T-ALL.

SUMMARY OF THE INVENTION

Taking these considerations into account, there is a need for innovative therapeutic solutions that effectively treat T-cell acute lymphoblastic leukemia.

In accordance with the present invention, the aforesaid object is achieved thanks to the solution specifically referred to in the attached claims, which form an integral part of the present description.

One embodiment of the present invention refers to compounds of formula (I) for use as compounds with anti-tumor activity for the treatment of T-cell acute lymphoblastic leukemia (T-ALL)

(I)

wherein

X and Y are carbon atoms bound by a single or double bond having, independently, an E or Z configuration;

$R_{1'}$ is hydrogen, halogen, $OR_A$, $C(=O)R_A$, $C(=O)OR_A$, $OC(=O)R_A$, $SR_A$, $SO_2R_A$, $SO_3R_A$, $OSO_2R_A$, $OSO_3R_A$, $N(R_A)_2$, $NHC(=O)R_A$, $C(=O)N(R_A)_2$, or $C(R_A)_3$;

$R_{2'}$, $R_{3'}$, $R_1$, $R_2$, $R_3$ are the same or different and independently selected from: hydrogen; halogen; $OR_B$; $C(=O)R_B$; $C(=O)OR_B$; $OC(=O)R_B$; $SR_B$; $SO_2R_B$; $SO_3R_B$; $OSO_2R_B$; $OSO_3R_B$; $N(R_B)_2$; $NHC(=O)R_B$; $C(=O)N(R_B)_2$; $C(R_B)_3$; a linear or branched, saturated or unsaturated $C_{1-7}$ acyclic aliphatic group optionally containing up to three heteroatoms independently selected from nitrogen, oxygen or sulfur; a $C_{5-7}$ cycloalkyl group; a phenyl group; a $C_{5-7}$ heterocyclic group;

wherein at each occurrence $R_A$ and $R_B$ are independently selected from: hydrogen; a linear or branched, saturated or unsaturated $C_{1-7}$ aliphatic group optionally containing up to three heteroatoms independently selected from nitrogen, oxygen or sulfur; a $C_{5-7}$ cycloalkyl group; a phenyl group; a $C_{5-7}$ heterocyclic group;

and pharmaceutically acceptable salts thereof.

BRIEF DESCRIPTION OF THE DRAWINGS

The invention will now be described in detail, by way of non-limiting example, with reference to the attached figures, wherein.

DETAILED DESCRIPTION OF THE INVENTION

In the following description, there are numerous specific details to provide a thorough understanding of the embodiments. The embodiments may be implemented, in practice, without one or more of the specific details, or with other methods, components, materials, etc. In other cases, well-known structures, materials or operations are not shown or described in detail to avoid obscuring certain aspects of the embodiments.

Throughout the present specification, the reference to "an embodiment" or "embodiment" means that a particular configuration, structure, or characteristic described in connection with the embodiment is included in at least one embodiment. Therefore, the appearance of expressions "in a certain embodiment" or "in an embodiment" in various points throughout this specification does not necessarily always refer to the same embodiment. Moreover, the particular details, structures or characteristics can be combined in any suitable way in one or more embodiments.

The headings used here are used merely for convenience, and do not interpret the object or meaning of the embodiments.

In recent years, scientific and industrial interest has been progressively increasing in relation to small naturally-occurring molecules, bio-pharmacologically active in various pathological contexts including neoplastic diseases. In this context, in addition to all the molecules proposed as gamma-secretase inhibitors, various naturally-occurring molecules have been proposed as potentially new anti-tumor agents capable of suppressing Notch signaling.

In the present study, a library of about one thousand naturally-occurring compounds, isolated from plants known for their use in traditional medicine, and their chemical derivatives, were grouped into clusters according to a chemo-informatics approach.

The clustering of the library according to this method allowed the obtainment of groups of chemically and pharmacologically similar molecules, for each of which a representative molecule (A-H) has been identified, illustrated in Table 1.

In order to detect small molecules able to modulate the Notch signal transduction pathway, the effects on the endogenous activation of Notch signaling and on cell proliferation in stabilized human lines of T-ALL were evaluated, known to be sensitive to the block of Notch signaling for each representative molecule of each of the eight clusters (A-H).

The cross-analysis of the results obtained from biochemical and functional assays indicated the molecule 3,4,2', 4'-tetrahydroxychalcone (butein, C) as a new and potent inhibitor of Notch signaling able to significantly inhibit cell proliferation at low concentrations. In this regard, the inventors of the present application have verified that short exposure times to the molecule C significantly repress both the proliferation and the endogenous activation of the Notch1 receptor starting from a concentration between 5 μM and 10 μM, with a dose-dependent effect in human T-ALL cell lines.

In order to enhance the activity and selectivity of action of butein (C), the present inventors have designed a number of structural analogues of butein, which have been synthesized and tested in vitro.

Analysis of the results obtained from biochemical and functional assays has shown that these compounds exhibit a good inhibitory capacity of Notch signaling and proliferation compared to butein itself, so that these compounds present a pharmacological potential for treating T-cell acute lymphoblastic leukemia.

In one embodiment, the present description concerns compounds of formula (I) as compounds with anti-tumor activity for the treatment of T-cell acute lymphoblastic leukemia (T-ALL)

wherein

X and Y are carbon atoms bound by a single or double bond having, independently, an E or Z configuration;

$R_{1'}$ is hydrogen, halogen, $OR_A$, $C(=O)R_A$, $C(=O)OR_A$, $OC(=O)R_A$, $SR_A$, $SO_2R_A$, $SO_3R_A$, $OSO_2R_A$, $OSO_3R_A$, $N(R_A)_2$, $NHC(=O)R_A$, $C(=O)N(R_A)_2$, or $C(R_A)_3$;

$R_{2'}$, $R_{3'}$, $R_1$, $R_2$, $R_3$ are the same or different and independently selected from: hydrogen; halogen; $OR_B$; $C(=O)R_B$; $C(=O)OR_B$; $OC(=O)R_B$; $SR_B$; $SO_2R_B$; $SO_3R_B$; $OSO_2R_B$; $OSO_3R_B$; $N(R_B)_2$; $NHC(=O)R_B$; $C(=O)N(R_B)_2$; $C(R_B)_3$; a linear or branched, saturated or unsaturated $C_{1-7}$ acyclic aliphatic group optionally containing up to three heteroatoms independently selected from nitrogen, oxygen or sulfur; a $C_{5-7}$ cycloalkyl group; a phenyl group; a $C_{5-7}$ heterocyclic group;

wherein, at each occurrence, $R_A$ and $R_B$ are independently selected from: hydrogen; a linear or branched, saturated or unsaturated $C_{1-7}$ aliphatic group optionally containing up to three heteroatoms independently selected from nitrogen, oxygen or sulfur; a $C_{5-7}$ cycloalkyl group; a phenyl group; a $C_{5-7}$ heterocyclic group;

and pharmaceutically acceptable salts thereof.

In one or more embodiments of the invention of the present description, X and Y are carbon atoms bound by a double bond in the compounds of formula (I).

In one or more embodiments of the invention subject of this description $R_{1'}$ is hydrogen, halogen, $OR_A$, $OC(=O)R_A$, $SR_A$, $R_A$, $SR_A$, $SO_2R_A$, $SO_3R_A$, $OSO_2R_A$, $OSO_3R_A$, $C(R_A)_3$; $R_{2'}$, $R_{3'}$, $R_1$, $R_2$, $R_3$ are the same or different and independently selected from: hydrogen; halogen; OR $OR_B$; $C(=O)R_B$; $C(=O)OR_B$; $OC(=O)R_B$; $SR_B$; $SO_2R_B$; $SO_3R_B$; $OSO_2R_B$; $OSO_3R_B$; $N(R_B)_2$; $NHC(=O)R_B$; $C(=O)N(R_B)_2$; $C(R_B)_3$; $R_A$ and $R_B$, at each occurrence, are independently selected from: hydrogen; a saturated or unsaturated aliphatic, linear or branched $C_{1-7}$ aliphatic group optionally containing up to three heteroatoms independently selected from nitrogen, oxygen and sulfur; a $C_{5-7}$ cycloalkyl group; a phenyl group; a $C_{5-7}$ heterocyclic group.

In one or more embodiments of the invention subject of the present description $R_{1'}$ is hydrogen, halogen, $OR_A$, $OC(=O)R_A$, $SR_A$, $SO_2R_A$, $SO_3R_A$, $OSO_2R_A$, $OSO_3R_A$, $C(R_A)_3$; $R_{2'}$, $R_{3'}$, $R_1$, $R_2$, $R_3$ are the same or different and independently selected from: a saturated or unsaturated, linear or branched $C_{1-7}$ acyclic aliphatic group optionally containing up to three heteroatoms independently selected from nitrogen, oxygen and sulfur; a $C_{5-7}$ cycloalkyl group; a phenyl group; a $C_{5-7}$ heterocyclic group, and $R_A$ assumes the meaning indicated above.

In one embodiment of the invention subject of the present description, X and Y are carbon atoms bound by a double bond with an E or Z configuration; $R_{1'}$ is $OR_A$; $R_{2'}$ is hydrogen; $R_{3'}$, $R_1$, $R_2$, are the same or different and independently selected from: hydrogen and $OR_B$; $R_3$ is $OR_B$; and $R_A$ and $R_B$, at each occurrence, are independently selected from: hydrogen; a linear or branched, saturated or unsaturated $C_{1-7}$ aliphatic group, preferably a linear or branched, saturated or unsaturated $C_{1-3}$ aliphatic group; a $C_{5-7}$ heterocyclic group.

A preferred embodiment of the invention subject of the present description concerns a compound selected from:

2',3,4,4'-tetramethoxychalcone (1)
2'-hydroxy-3,4,4'-trimethoxychalcone (2)
2'-hydroxy-4,4'-dimethoxychalcone (3)
2',4,4'-trimethoxychalcone (4)
2'-hydroxy-4,4'-dimethoxy-3-(tetrahydropyran-2-yloxy)chalcone (5a)
2',3-dihydroxy-4,4'-dimethoxychalcone (5)
2'-hydroxy-3,4-dimethoxy-4'-(tetrahydropyran-2-yloxy)chalcone (6a)
2'-hydroxy-3,4'-dimethoxy-4-(tetrahydropyran-2-yloxy)chalcone (7a)
2',4-dihydroxy-3,4'-dimethoxychalcone (7)
2'-hydroxy-4'-methoxy-4-(tetrahydropyran-2-yloxy)chalcone (8a)
2',4-dihydroxy-4'-methoxychalcone (8)
2',4-dihydroxy-4'-methoxydihydrochalcone (8b)
2'-hydroxy-4'-methoxychalcone (9)
2'-hydroxy-3,4'-dimethoxychalcone (10)
2'-hydroxy-4'-methoxy-3-(tetrahydropyran-2-yloxy)chalcone (11a)
2',3-dihydroxy-4'-methoxychalcone (11)
2,2'-dihydroxy-4'-methoxychalcone (12)
2'-hydroxy-2,4-dimethoxychalcone (13)
2'-hydroxy-4-(tetrahydropyran-2-yloxy)chalcone (14a)
2',4-dihydroxychalcone (14)
2'-methoxy-4-(tetrahydropyran-2-yloxy)chalcone (15a)
4-hydroxy-2'-methoxychalcone (15)
2',4'-dimethoxy-4-(tetrahydropyran-2-yloxy)chalcone (16a)
4-hydroxy-2',4'-dimethoxychalcone (16)
4'-methoxy-4-(tetrahydropyran-2-yloxy)chalcone (17a)
4-hydroxy-4'-methoxychalcone (17).

In an additional embodiment, the present description relates to a pharmaceutical composition comprising at least one compound of formula (I), as defined above, and at least one pharmaceutically acceptable excipient or vehicle.

In a different embodiment, the present description relates to compounds of formula (I)

wherein

X and Y are carbon atoms bound by a single or double bond having, independently, an E or Z configuration;

$R_{1'}$ is hydrogen, halogen, $OR_A$, $C(=O)R_A$, $C(=O)OR_A$, $OC(=O)R_A$, $SR_A$, $SO_2R_A$, $SO_3R_A$, $OSO_2R_A$, $OSO_3R_A$, $N(R_A)_2$, $NHC(=O)R_A$, $C(=O)N(R_A)_2$, or $C(R_A)_3$;

$R_{2'}$, $R_{3'}$, $R_1$, $R_2$, $R_3$ are the same or different and independently selected from: hydrogen; halogen; $OR_B$; $C(=O)R_B$; $C(=O)OR_B$; $OC(=O)R_B$; $SR_B$; $SO_2R_B$; $SO_3R_B$; $OSO_2R_B$; $OSO_3R_B$; $N(R_B)_2$; $NHC(=O)R_B$; $C(=O)N(R_B)_2$; $C(R_B)_3$; a linear or branched, saturated or unsaturated $C_{1-7}$ acyclic aliphatic group optionally containing up to three heteroatoms independently selected from nitrogen, oxygen or sulfur; a $C_{5-7}$ cycloalkyl group; a phenyl group; a $C_{5-7}$ heterocyclic group;

wherein, at each occurrence, $R_A$ and $R_B$ are independently selected from: hydrogen; a linear or branched, saturated or unsaturated $C_{1-7}$ aliphatic group optionally containing up to three heteroatoms independently selected from nitrogen, oxygen or sulfur; a $C_{5-7}$ cycloalkyl group; a phenyl group; a $C_{5-7}$ heterocyclic group;

and relative salts, preferably pharmaceutically acceptable salts.

In general, the data of the present invention propose butein and synthetic chalcones of formula (I), butein analogues, as inhibitors of Notch signaling, and emphasize the efficacy of compound 8 as a new potential antitumor agent that blocks Notch signaling. In this regard, short-term treatment with compound 8 represses cell proliferation, protein expression of activated domains of Notch1 and Notch3 receptors, and the gene expression of several known transcriptional targets of the Notch pathway at lower concentrations than the molecule C in different T-ALL cellular models.

In this regard, it should be noted that in European patent application EP 2606884, small molecule inhibitory compounds of Notch are disclosed, although these compounds exhibit inhibitory activity comparable to that of compound 8, the latter has a significantly lower molecular weight. Given that the efficiency of a candidate drug is given by the relationship between the biological activity and the molecular weight (or the number of heavy atoms), compound 8 is considerably more efficient, being further validated by SAR studies. The patent application US-A-2015/0175548 discloses a molecule similar to nifedipine, with comparable anti-proliferative activity, albeit slightly less efficient, to that of compound 8. It should be noted that nifedipine is a calcium channel blocker, with effects on cardiac activity, so that its use in therapy is doubtful given the potential relevance of the side effects it may cause, particularly on the heart.

In a recent study, the molecule Xanthohumol has been described as a Notch signaling inhibitor and apoptosis promoter in hepatocarcinoma cells with $IC_{50}$, on average, between 10 and 15 µM (Kunnimalaiyaan et al., 2015). Compound 8, although structurally related to the molecules described by Kunnimalaiyaan and colleagues, was shown to be significantly more active. It should be noted that, in addition to that reported, in the screening carried out by the present inventors, the chalcones of formula (I) prenylated in ring A, although the prenylation position was different from that of the compound being disclosed, did not show any inhibitory activity of Notch (4-OH-Isocordoin).

RESULTS

Butein: Naturally-Occurring Chalcone as an Inhibitor of the Notch Signal Transduction Pathway To focus attention on a relatively small, manageable number of molecules of the library of natural products, only the molecules most representative of the eight most abundant clusters were considered for in vitro tests. For this purpose, a diversity-oriented random selection (DORS) approach was used of the compounds based on a clustering algorithm that is based on the substructure and molecular fingerprint similarity (Stahl and Mauser, 2005). Representative molecules of the eight clusters are shown in Table 1.

TABLE 1

Structure and inhibitory activity of the natural compounds A-H.
The values of $IG_{50}$ were calculated for 36-hour treatments in DND41 cells.
The reported values represent the mean of triplicate experiments ± S.D.

| Compound | Chemical structure | IG50 S.D. (µg) |
|---|---|---|
| A | | >50 |
| B | | 13.89<br>2.70 |
| C | | 7.79<br>1.73 |

TABLE 1-continued

Structure and inhibitory activity of the natural compounds A-H.
The values of $IG_{50}$ were calculated for 36-hour treatments in DND41 cells.
The reported values represent the mean of triplicate experiments ± S.D.

| Compound | Chemical structure | IG50 S.D. (µg) |
|---|---|---|
| D |  | >50 |
| E |  | >50 |
| F |  | >50 |
| G |  | >50 |
| H |  | 22.64 1.89 |

In order to identify new naturally-occurring molecular agents able to modulate Notch signaling, the effects on protein expression of the activated domain of Notch1 (N1VAL), and of the intracellular domain of Notch3 (N3ICD), were evaluated in DND41 cells through Western blotting assays, following treatment for 36 hours with increasing concentrations (0, 1, 5, 10, 20, 50 µM) of the eight molecules (A-H) previously selected. Functional biochemical screening was performed on T-ALL DND41 cells because they are notoriously sensitive to the block of Notch signaling, and characterized by the constitutive and ligand-independent activation of the Notch1 pathway and by the high expression of Notch3. This makes this cell line a useful experimental model for screening putative Notch inhibitors.

Figure 1:
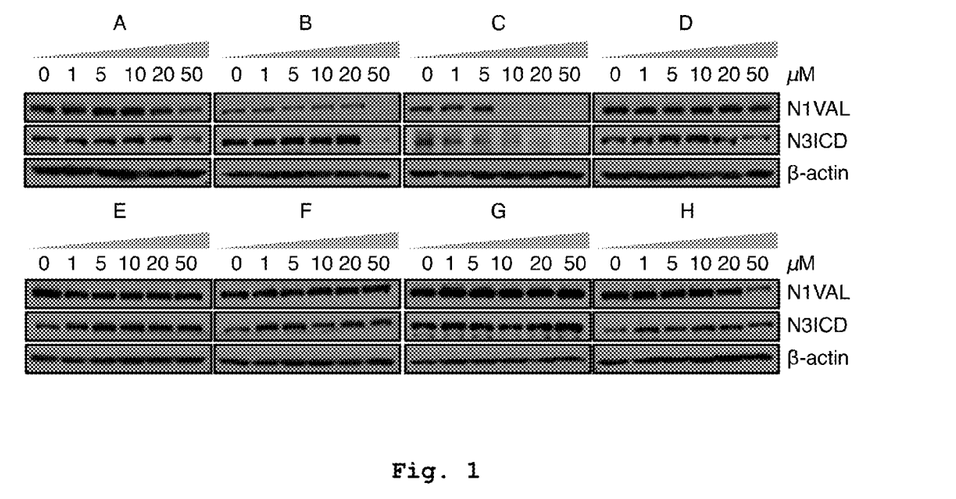
FIG. 1. Chalcone C inhibits endogenous Notch signaling in T-ALL DND41 cells. Protein expression of the activated domain of Notch1 (N1VAL), of the intracellular domain of Notch3 (N3ICD) and of β-actin in DND41 cells in response to 36 hours of treatment at increasing concentrations of eight molecules (designated as A-H) representative of a library of about 1000 different compounds.

Among the eight molecules considered, molecule C revealed the highest inhibitory activity against Notch signaling, as shown by the decreased expression of N1VAL and N3ICD at concentrations ranging from 5 µM to 10 µM (FIG. 1). On the other hand, treatments with the molecules D, E, F and G did not significantly modulate the expression of N1VAL, while A, B and H reduce its expression at very high concentrations (between 20 µM and 50 µM) (FIG. 1).

In order to evaluate the biological implications of the compounds, their effect on cell proliferation/vitality was tested by determining the relative concentrations of growth inhibition ($IG_{50}$) by means of the MTS cellular assay. Consistent with the high inhibitory activity of Notch, exposure to molecule C dramatically reduces cell proliferation in DND41 cells at concentrations comparable to those sufficient to inhibit Notch signaling ($IG_{50}$ of 7.79±1.73 µM) (Table 1). Conversely, compounds B and H show a low anti-proliferative activity with $IG_{50}$ values of 13.89±2.70 µM and 22.64±1.89 µM, respectively, while the molecules A, D, E, F and G do not significantly affect cell proliferation at doses of up to 50 µM. Overall, cross-analysis of the screening data described above indicates that among all the natural compounds considered, chalcone C (butein) is the most potent inhibitor of Notch signaling and cell proliferation in T-ALL cells.

Design and Synthesis of Butein Derivatives

Figure 2:
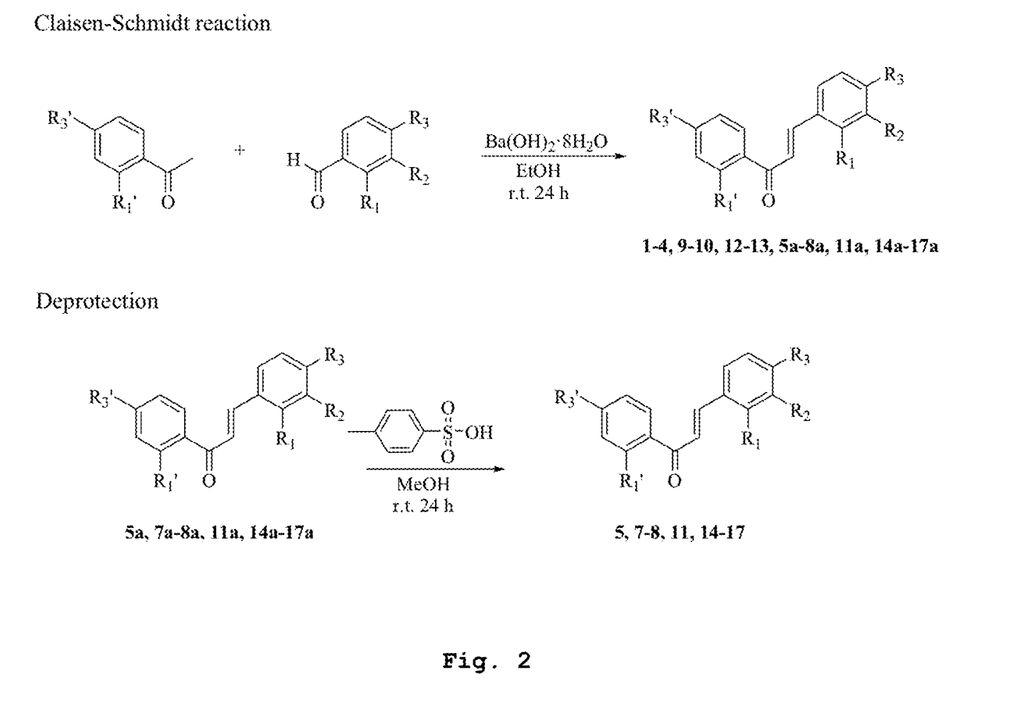
FIG. 2. General scheme for the synthesis of compounds 1-17. Claisen-Schmidt condensation was used to prepare the chalcone scaffold. The compounds 5a, 7a-8a, 11a and 14a-17a were subsequently deprotected to form their respective chalcones.
Figure 3:
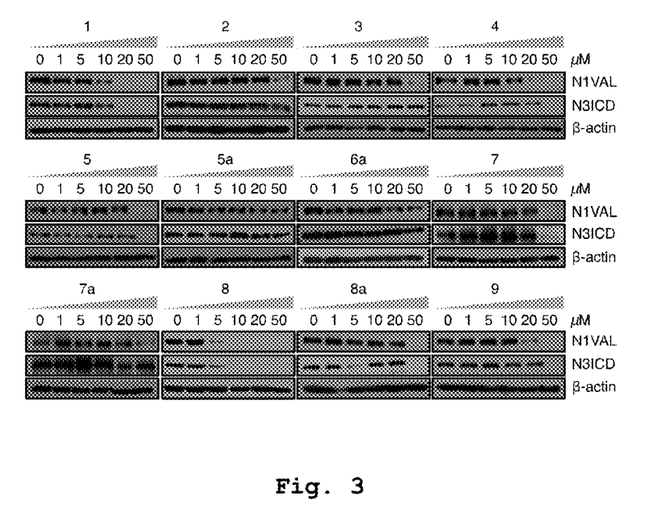
FIG. 3. Compound 8 is a potent inhibitor of Notch signaling in DND41 cells. Protein expression levels of N1VAL, N3ICD and β-actin in DND41 cells in response to 36 hours of treatment at increasing concentrations of 12 synthetic derivatives of chalcone C (named 1, 2, 3, 4, 5, 5a, 6a, 7, 7a, 8, 8a and 9).

Results from the biological tests have suggested the promising role of the chalcone scaffold in modulating the Notch signaling pathway. Given that molecule C emerged from the first screening as a promising hit, a second generation of chemical derivatives (Table 2) was designed and synthesized in order to increase the biological activity, to remove the catecholic group (Schweigert et al., 2001) that is very sensitive to oxidation reactions, and to outline the structure-activity relationships (SAR). The general synthetic strategy used to prepare chalcones is based on the Claisen-Schmidt condensation (FIG. 2) (Sogawa et al., 1994).

tions than butein (doses between 1 μM and 5 μM) (FIG. 3). Conversely, all the other 11 synthetic derivatives modulate the expression levels of the two receptor domains at higher concentrations (FIG. 3). In support of the high inhibitory activity of Notch, cell proliferation assays in response to increasing doses of the synthetic compounds demonstrated that compound 8 is the most potent repressor of proliferation. Treatments with compound 8 repress proliferation with $IG_{50}=1.92$ μM±0.14 μM, while all the other chemical derivatives present anti-proliferative activities that are 10 to 20 times weaker, as demonstrated by $IG_{50}$ values greater than 11 μM (Table 1). Given the high power of action at low micromolar concentrations of compound 8, subsequent functional and biological comparison analyses between compound 8 and the additional 14 compounds illustrated in

TABLE 2

Structure and inhibitory activity of synthetic derivatives of chalcone C (1-17).
The $IG_{50}$ values were calculated for 36-hour treatments in DND41 cells.
The reported values represent the mean of triplicate experiments ± S.D.

(II)

| Compound | $R_{1'}$ | $R_{3'}$ | $R_1$ | $R_2$ | $R_3$ | X—Y[a] | $IG_{50}$ ± S.D. (μM) |
|---|---|---|---|---|---|---|---|
| 1 | OCH₃ | OCH₃ | H | OCH₃ | OCH₃ | CH=CH | 15.04 ± 3.04 |
| 2 | OH | OCH₃ | H | OCH₃ | OCH₃ | CH=CH | 30.96 ± 5.98 |
| 3 | OH | OCH₃ | H | H | OCH₃ | CH=CH | 47.50 ± 1.14 |
| 4 | OCH₃ | OCH₃ | H | H | OCH₃ | CH=CH | 14.41 ± 2.56 |
| 5a | OH | OCH₃ | H | OTHP | OCH₃ | CH=CH | >50 |
| 5 | OH | OCH₃ | H | OH | OCH₃ | CH=CH | 36.24 ± 10.61 |
| 6a | OH | OTHP | H | OCH₃ | OCH₃ | CH=CH | >50 |
| 7a | OH | OCH₃ | H | OCH₃ | OTHP | CH=CH | 24.44 ± 1.76 |
| 7 | OH | OCH₃ | H | OCH₃ | OH | CH=CH | 33.10 ± 1.89 |
| 8a | OH | OCH₃ | H | H | OTHP | CH=CH | 48.52 ± 3.42 |
| 8b | OH | OCH₃ | H | H | OH | CH₂—CH₂ | >50 |
| 8 | OH | OCH₃ | H | H | OH | CH=CH | 1.92 ± 1.04 |
| 9 | OH | OCH₃ | H | H | H | CH=CH | 11.11 ± 0.59 |
| 10 | OH | OCH₃ | H | OCH₃ | H | CH=CH | 21.32 ± 1.72 |
| 11a | OH | OCH₃ | H | OTHP | H | CH=CH | 17.35 ± 1.2 |
| 11 | OH | OCH₃ | H | OH | H | CH=CH | 13.62 ± 1.76 |
| 12 | OH | OCH₃ | OH | H | H | CH=CH | 14.23 ± 0.58 |
| 13 | OH | OCH₃ | OCH₃ | H | H | CH=CH | 21.76 ± 1.78 |
| 14a | OH | H | H | H | OTHP | CH=CH | 48.58 ± 3.42 |
| 14 | OH | H | H | H | OH | CH=CH | 16.47 ± 0.90 |
| 15a | OCH₃ | H | H | H | OTHP | CH=CH | 31.52 ± 1.46 |
| 15 | OCH₃ | H | H | H | OH | CH=CH | 16.82 ± 2.71 |
| 16a | OCH₃ | OCH₃ | H | H | OTHP | CH=CH | 32.57 ± 0.92 |
| 16 | OCH₃ | OCH₃ | H | H | OH | CH=CH | 13.82 ± 0.61 |
| 17a | H | OCH₃ | H | H | OTHP | CH=CH | 28.76 ± 0.29 |
| 17 | H | OCH₃ | H | H | OH | CH=CH | 19.50 ± 0.56 |

Compound 8 is a Potent Inhibitor of Notch and Proliferation in T-ALL Cells.

In order to investigate the activity and selectivity of action of the 12 synthetic derivatives of butein, and following the screening scheme described in the first design phase, the efficacy of these molecules was analyzed by verifying the effects of 36 hours of treatment at increasing doses on the activation of Notch signaling and on the proliferation in DND41 cells.

Figure 4:
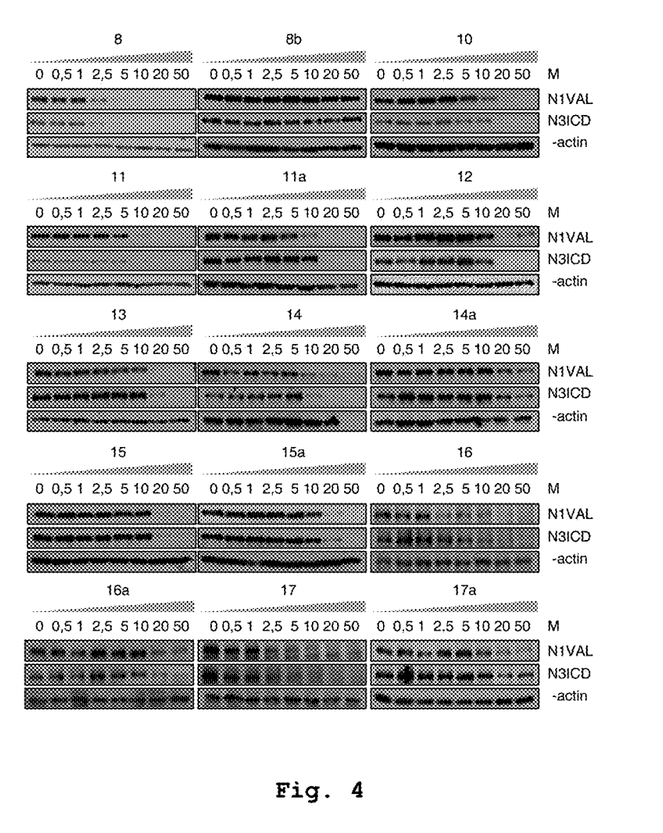
FIG. 4. The synthetic derivatives of compound 8 reveal low levels of inhibitory activity of Notch signaling. Protein expression levels of N1VAL, N3ICD and β-actin in DND41 cells in response to 36 hours of treatment at increasing concentrations of compound 8 and its 14 synthetic derivatives (named 8b, 10, 11, 11a, 12, 14, 14a, 15, 15a, 16a, 17 and 17a).
Figure 5:
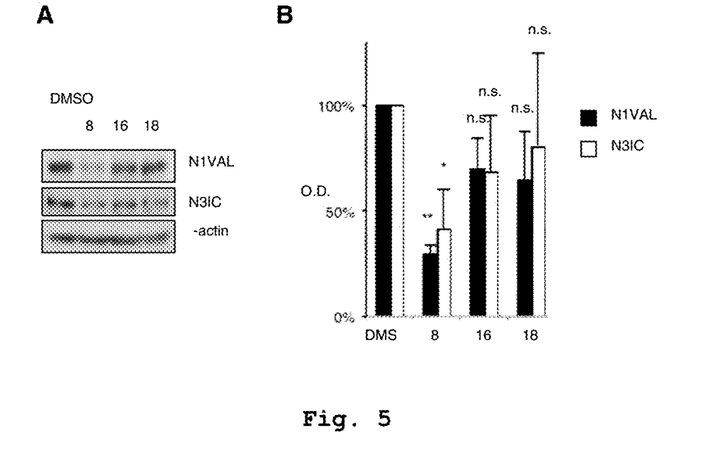
FIG. 5. Compound 8 is the most potent inhibitor of Notch signaling among the synthetic derivatives of C taken into consideration (A) Western blot representatives (B) and relative densitometric quantifications (OD) of N1VAL, N3ICD and β-actin expression levels in DND41 cells in response to 36 hours of treatment with 2.5 μM of compounds 8, 16 or 17. The data shown in the graph represent the means values±standard deviations of three independent experiments. *$P<0.05$; $P<0.01$; n.s. not significant.

Treatments with compound 8 inhibit the expression of Notch1 and Notch3 activated domains at lower concentra- Table 2 were carried out by adding two intermediate concentrations (0.5 μM and 2.5 μM) in dose-response assays (0, 0.5, 1, 2.5, 5, 10, 20, 50 μM). Among the 14 compounds of Table 2, only molecules 16 and 17 showed inhibitory activity of Notch signaling in a range of concentrations comparable to those disclosed for compound 8 (at doses of 2.5 μM) (FIG. 4). The subsequent comparative analysis of the effects of 36 hours of treatment with compounds 8, 16 and 17 on the protein expression of N1VAL and N3ICD finally confirmed compound 8 as the most potent Notch inhibitor (FIG. 5). In addition, compound 8 is the most effective antiproliferative agent compared to all the synthetic derivatives tested, including 16 and 17, which reveal $IG_{50}$ values greater than 13 μM (Table 2).

Figure 6:
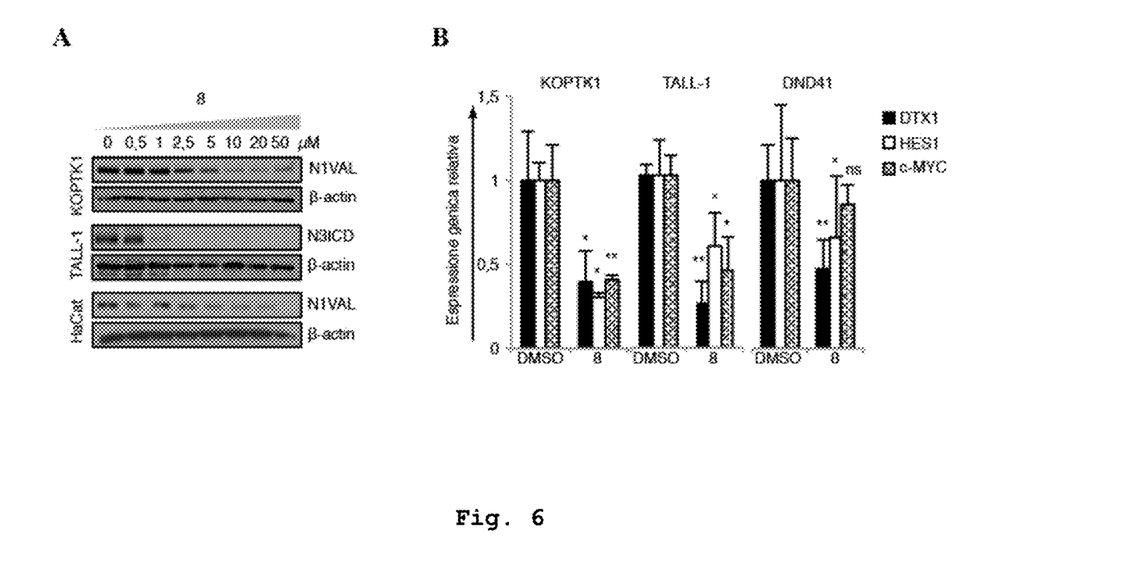
FIG. 6. Compound 8 represses Notch signaling in cellular contexts of T-ALL (A) Protein expression levels of N1VAL and β-actin in KOPTK1 cells and in HaCat cells and protein expression of N3ICD and β-actin in TALL-1 cells in response to 36 hours of treatment at increasing concentrations of compound 8 (B) Gene expression levels of DELTEX1 (DTXI), HES1 and c-MYC in response to 36 hours of exposure to 2.5 μM of compound in KOPTK1 and DND41 cells, and in response to 36 hours of exposure to 1 μM of compound 8 in TALL-1 cells. The data shown represent the mean values of three independent experiments, standardized with respect to GAPDH expression±standard deviations.

Overall, the data obtained in the experiment described above propose compound 8 as the most promising Notch blocking agent among all the molecules tested, and in order to exclude possible specific cell line effects, analysis was also carried out on additional cell lines. As confirmation of its efficacy on the inhibition of Notch signaling, 36 hours of treatment with compound 8 reduced N1VAL expression levels in KOPTK1 cells and N3ICD in TALL-1 cells, in a dose-dependent manner (FIG. 6A). The KOPTK1 cell line is characterized by constitutive Notch1 activation, due to gene mutations of Notch1, while the TALL-1 cell line, due to mutations of the Notch3 gene, has constitutively active signaling of the Notch3 receptor.

In line with the block of signaling, treatment with compound 8 in DND41, KOPTK1 and TALL-1 cells significantly reduces the expression of known Notch gene targets such as DELTEX1, HES1e and c-MYC (FIG. 6B). In addition, in the same lines, compound 8 drastically inhibits cell proliferation with $IC_{50}$=0.91±0.06 μM in KOPTK1 cells and with $IC_{50}$=0.29±0.02 μM in TALL-1 cells.

Conversely, exposure to compound 8 does not significantly influence the proliferation of immortalized non-tumor lines of HaCaT keratinocytes ($IC_{50}$=48.61±8.06 μM), in which Notch acts as an oncosupressor. Confirming instead the Notch blocking activity, treatment with compound 8 in the same cells significantly reduces the expression of the activated domain of Notch1 starting from concentrations of 2.5 μM (FIG. 6A).

Structure-activity Relationships (SARs) of Chalcone Derivatives

Figure 7:
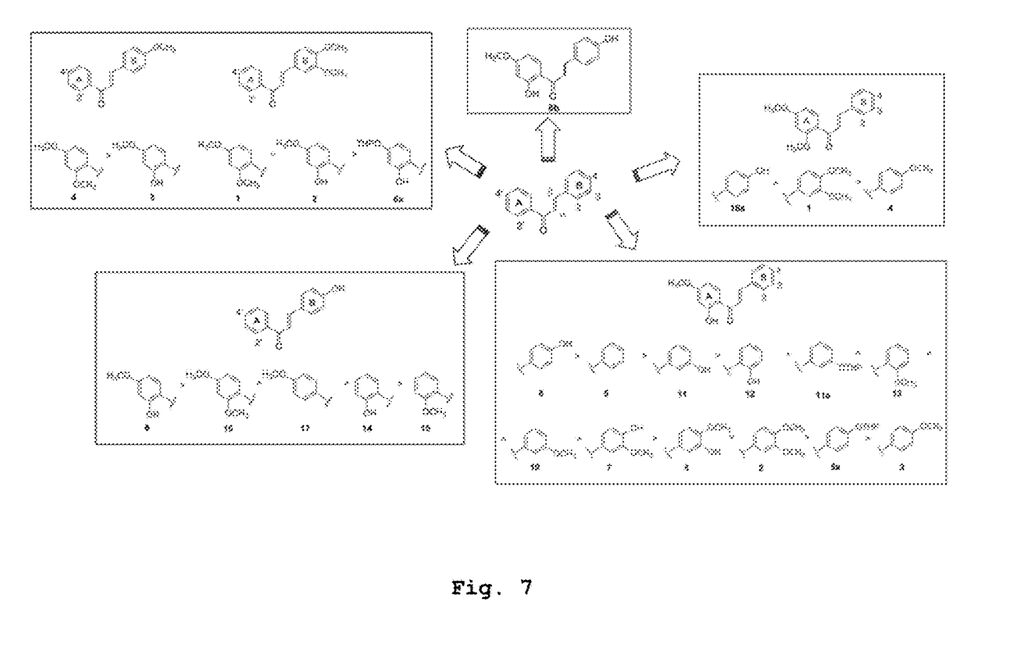
FIG. 7. Graphical representation of the SAR of the chalcone derivatives as Notch inhibitors in T-ALL. Analysis of the results obtained from the biological tests allowed identification of three structural levels for the SAR: ring A, ring B and the α, β-unsaturated carbonyl system of the chalcone scaffold.

Biological analyzes of the natural chalcone C and of the compounds of formula (I) highlight compound 8 as the most active Notch inhibitor in T-ALL. The SAR was processed and graphically represented (FIG. 7), based on three structural levels of the chalcone base skeleton: ring A, ring B and the α,β-unsaturated carbonyl system.

Regarding ring A, methylation of the hydroxyl group at position 2' improves the inhibitory effect on cell proliferation, only when ring B is not replaced by hydroxyl groups at position 4. Under these conditions, the presence of the methoxyl group at position 4' provides a greater activity with respect to the steric mole of the tetrahydropyranyl protecting group. Therefore, it is apparent from the structure of compound 8 that the hydroxylic substitutions act synergically at positions 2' and 4 of the chalcone scaffold. Based on this evidence, the single replacement on ring A (14, 15 and 17) at different positions reduces biological activity with respect to the rings with double replacement at position 2' and 4' (8 and 16). In addition, single-replacement derivatives have shown a comparable inhibitory effect on cell proliferation, although methylation of the hydroxyl group at position 4' dramatically reduces the expression levels of N1VAL and N3ICD with respect to compound 8, unlike that observed for chalcones with a single-replacement at position 2' (14 and 15).

In particular, the activity of chalcone derivatives seems to be significantly dependent on the replacement of ring B. Indeed, comparing the chalcones having the same ring A, the hydroxyl group improves the biological activity, particularly when inserted at position 4, playing a key role in reducing both cell proliferation activity and Notch expression (8).

Finally, reducing the double bond of the α,β-unsaturated carbonyl system completely abolishes the biological efficacy, suggesting that the reduced molecular flexibility required to ensure the distance between the phenyl rings A and B is more suitable for inducing Notch inhibition.

Materials and Methods

Chemoinformatics A clustering algorithm similar to that previously developed by Stahl and Mauser (Stahl and Mauser, 2005) was generated and used, exploiting the modularity and versatility of the Python scripting language (OpenEye Python Toolkit [OpenEye Toolkits 2015. OpenEye Scientific Software, Santa Fe, N. Mex. http://www.eyesopen.com]). The algorithm was then used to cluster the molecules of the in-house library of naturally-available compounds. A threshold value of 0.6 for the Tanimoto comparison of the maccs166-type fingerprints, while a threshold value of 0.8 was used to compare the Raymond's score (Raymond et al., 2002) during the analysis and comparison of the substructures of the various molecules (Stahl and Mauser, 2005).

Characterization of the Naturally-occurring Compounds A-H

All the tested compounds A-H come from the library of natural products of the laboratory of Prof. Botta.

The chemical identity of the compounds tested is known and was verified by Nuclear Magnetic Resonance (NMR), the results obtained were in accordance with those reported in the literature.

The purity of compounds A, B, E and F was greater than 95% and was analyzed using reverse phase HPLC, the chromatographic conditions are reported below.

Compound A (taxifolin or (2R,3R)-2-(3,4-dihydroxyphenyl)-3,5,7-trihydroxy-2,3-dihydrochromen-4-one) NMR analysis was consistent with that reported in the literature (Yang et al., 2015).

Compound B (4-hydroxy-isocordoin or (E)-1-[2,4-dihydroxy-3-(3-methylbut-2-enyl)phenyl]-3-(4-hydroxyphenyl)prop-2-en-1-one) NMR analysis was consistent with that reported in the literature (Monache et al., 1974).

Compound C (butein or (E)-1-(2,4-dihydroxyphenyl)-3-(3,4-dihydroxyphenyl)prop-2-en-1-one) (Chokchaisiri et al., 2009) was purchased from Sigma-Aldrich (487-52-5), and was used without further modifications.

Compound D (xantotoxin or 9-methoxyfuran[3,2-g]chromen-7-one (Compagnone and Rodriguez, 1993; Rashid et al., was purchased from Sigma-Aldrich (298-81-7), and was used without further modifications.

Compound E (columbianetin or (8R)-8-(2-hydroxypropane-2-yl)-8,9-dihydrofuran[2,3-h]chromen-2-one) NMR analysis was consistent with that reported in the literature (Cuca L E and Delle Monache, 1998).

Compound F (1-hydroxy-7-methoxy-9H-xanthen-9-one) NMR analysis was consistent with that reported in the literature (Delle Monache et al., 1983).

Compound G (usnic acid or 2,6-diacetyl-7,9-dihydroxy-8,9b-dimethyldibenzofuran-1,3-dione) (Studzinska-Srokaal et al., 2015) was purchased from Sigma-Aldrich (7562-61-0), and was used without further modifications.

Compound H (galangin or 3,5,7-trihydroxy-2-phenylchromen-4-one) (Zhong et al.) was purchased from Sigma-Aldrich (548-83-4), and was used without further modifications.

Synthesis Methods

All the reagents are commercially available and were used without further purification.

Silica gel (230-400 mesh) was used for purification by column gravity chromatography. All reactions were monitored by thin layer chromatography (TLC) and F254 fluorescence silica gel plates (Sigma-Aldrich 99569) were used. Melting points were determined with a Buchi Melting Point B-454 apparatus. The spectra $^1$H and $^{13}$C NMR were registered using an Ultra Shield™ Bruker 400 instrument (400 MHz for $^1$H NMR and 100 MHz for $^{13}$C NMR) using tetramethylsilane (TMS) as a standard. Chemical shifts are reported in parts per million (ppm). Multiplicities were reported as follows: singlet (s), doublet (d), triplet (t) and multiplet (m). Mass spectrometry was performed with the Thermo Finnigan LXQ linear ion trap mass spectrometer, equipped with electrospray ionization (ESI). High resolution mass spectra (HR-MS) were recorded with a Bruker Bio-Apex Fourier transform ion cyclotron resonance (FT-ICR).

General Method for the Protection of 3- and 4-hydroxybenzaldehyde as Tetrahydropyranil Ethers.

3- or 4-hydroxybenzaldehyde (16 mmol) and the pyridinium p-toluene-sulfonate (0.40 mmol) (Sigma-Aldrich 232238) were solubilized in $CH_2Cl_2$ (dichloromethane) (75 ml). Dissolution of the reagents was carried out by magnetic stirring and, thereafter, a solution of 3,4-dihydro-α-pyran (2.23 ml, 0.5 mmol) (Sigma-Aldrich 37350) in $CH_2Cl_2$ (75 ml) was slowly added. The reaction was maintained with stirring at room temperature for about 24 hours; a series of washes was then carried out with distilled water, dehydration was carried out with $Na_2SO_4$ and the solvents were evaporated under vacuum. The residue was purified on a flash chromatography column using an eluent mixture of n-hexane: EtOAc=9:1 (v/v), to obtain the corresponding tetrahydropyranyloxybenzaldehyde (precursor of 5a, 7a, 8a, 11a, 14a, 15a, 16a, 17a).

General Procedure for the Protection of 4'-hydroxyacetophenone as Tetrahydropyranyl Ether.

4'-hydroxyacetophenone (16 mmol) and the pyridinium p-toluenesulfonate (0.40 mmol) were solubilized in $CH_2Cl_2$ (75 mL). Dissolution of the reagents was carried out by magnetic stirring and, thereafter, a solution of 3,4-dihydro-α-pyran (2.23 ml, 0.5 mmol) in $CH_2Cl_2$ (75 ml) was slowly added. The reaction was maintained with stirring at room temperature for about 24 hours; a series of washes was then carried out with distilled water, dehydration was carried out with $Na_2SO_4$ and the solvents were removed under vacuum. The residue was purified on a flash chromatography column using an eluent mixture of n-hexane: EtOAc=9:1 (v/v), to obtain the corresponding tetrahydropyranyloxyacetophenone.

General Procedure for the Claisen-Schmidt Reaction

Barium hydroxide octahydrate [$Ba(OH)_2·8H_2O$] was slowly added to a solution of the corresponding acetophenone (0.01 mmol) and the corresponding benzaldehyde (0.01 mmol) in EtOH (ethanol). The reaction was stirred, at room temperature for about 24 hours and then concentrated under vacuum. Subsequently, distilled water was added, the mixture was neutralized with 2N HCl and extracted with EtOAc (ethyl acetate). The organic fraction was dehydrated with $Na_2SO_4$ and the solvents were then removed under vacuum. The residue was purified on a flash chromatography column using an eluent mixture of n-hexane: EtOAc=9:1 (v/v) to obtain the corresponding chalcone 1-4, 9-10, 12-13, 5a-8a, 11a, 14a-17a.

General Procedure for Deprotection of Chalcones

The protected chalcones 5a, 7a-8a, 11a, 14a-17a (0.25 mmol) and p-toluenesulfonic acid (0.03 mmol) were solubilized in MeOH (20 ml). The reaction was stirred, at room temperature, for about 24 hours and the solvent was removed under vacuum. Subsequently, distilled water was added, the mixture was neutralized with 5% $NaHCO_3$ and extraction with EtOAc was carried out. The organic fraction was isolated, dehydration was carried out with $Na_2SO_4$ and the solvents were then removed under vacuum. The residue was purified on a flash chromatography column using an eluent mixture of n-hexane: EtOAc=9:1 (v/v) to obtain the corresponding chalcone 5, 7-8, 11, 14-18.

Catalytic Hydrogenation of 8

Inside the reaction tube, two empty/nitrogen cycles were performed, and then compound 8 (100 mg, 0.37 mmol) was placed with 10% Pd/C (98 mg) in EtOAc (10 mL) at room temperature, at 1 atm pressure of $H_2$ for 24 hours. The reaction mixture was filtered through a membrane filter (Millipore, Millex-LH, 0.45 mm) and the filtrate was concentrated to obtain compound 8b with a quantitative yield.

Characterization of the Compounds of Table 2 2',3,4,4'-tetramethoxychalcone (1)

yellow solid (85% yield); pf 71.9-73.3° C. $^1$H NMR (400 MHz, CDCl$_3$): δ 7.72 (H-6', 1H, d), δ 7.61 (C$_β$H, 1H, d, J=16.0 Hz), δ 7.35 (C$_α$H—CO, 1H, d, J=16.0 Hz), δ 7.18 (H-6, 1H, dd, J=8.4 Hz e J=1.6 Hz), δ 7.11 (H-2, 1H, d, J=2.6 Hz), δ 6.87 (H-5, 1H, d, J=8.4 Hz), δ 6.56 (H-5', 1H, dd, J=8.4 Hz and J=2.0 Hz), δ 6.50 (H-3', 1H, d, J=2 Hz), δ 3.92 (OCH$_3$, 3H, s), δ 3.92 (OCH$_3$, 3H, s), δ 3.90 (OCH$_3$, 3H, s), δ 3.87 (OCH$_3$, 3H, s). $^{13}$C NMR (100 MHz, CDCl$_3$): δ 190.73, δ 163.94, δ 160.20, δ 150.97, δ 149.14, δ 142.43, δ 132.66, δ 128.44, δ 125.32, δ 122.61, δ 122.46, δ 111.12, δ 110.27, δ 105.09, δ 98.75, δ 55.97, δ 55.75, δ 55.53.

HRMS (ESI-FT-ICR) m/z: [M+H] calculated $C_{19}H_{21}O_5$ 329.13852 (monoisotopic mass), found 329.13857; [M+Na]$^+$ calculated $C_{19}H_{20}O_5Na$ 351.12029 (monoisotopic mass), found 351.11879.

2'-hydroxy-3,4,4'-trimethoxychalcone (2)

yellow solid (50% yield); pf 157.8-158.3° C. $^1$H NMR (400 MHz, CDCl$_3$): δ 13.54 (OH, 1H, s), δ 7.85 (C$_β$H, 1H, d, J=15.6 Hz), δ 7.86 (H-6', 1H, d), δ7.44 (C$_α$H—CO, 1H, d, J=16.0 Hz), δ 7.25 (H-6, 1H, dd, J=8.1 Hz and J=6 Hz), δ 7.16 (H-2, 1H, d, J=2 Hz), δ 6.91 (H-5, 1H, d, J=8.4 Hz), δ 6.51-6.47 (H3' and H-5', 2H, m), δ 3.97 (OCH$_3$, 3H, s). δ 3.94 (OCH$_3$, 3H, s), δ 3.86 (OCH$_3$, 3H, s). $^{13}$C NMR (100 MHz, CDCl$_3$): δ 191.80, δ 166.67, δ 166.08, δ 151.61, δ 149.31, δ 144.59, δ 131.13, δ 127.81, δ 123.33, δ 118.05, δ 114.14, δ 111.18, δ 110.26, δ 107.66, δ 101.06, δ 56.03, δ 55.59, δ 53.42.

HRMS (ESI-FT-ICR) m/z: [M+H]$^+$ calculated $C_{18}H_{19}O_5$ 315.12270 (monoisotopic mass), found 315.12313; [M+Na]$^+$ calculated $C_{18}H_{18}O_5Na$ 377.10464 (monoisotopic mass), found 337.10489.

2'-hydroxy-4,4'-dimethoxy Chalcone (3)

yellow solid (25% yield); pf 133.4-134.2° C. $^1$H NMR (400 MHz, CDCl$_3$): δ 13.56 (OH, 1H, s), δ 7.87 (C$_{62}$ H, 1H, d, J=15.6 Hz,), δ 7.84 (H-6', 1H, d, J=8 Hz), δ 7.62 (H-2 and H-6, 2H, d, J=8.8 Hz), δ 7.47 (C$_α$H—CO, 1H, d, J=15.6 Hz), δ 6.95 (H-3 and H-5, 2H, d, J=8.8 Hz), δ 6.50-6.48 (H-3' and H-5', 2H, m); δ 3.87 (OCH$_3$, 3H, s); δ 3.86 (OCH$_3$, 3H, s). $^{13}$C NMR (100 MHz, CDCl$_3$): δ 191.90, δ 166.64, δ 166.05, δ 161.82, δ 144.28, δ 131.12, δ 130.37, δ 127.56, δ 117.85, δ 114.48, δ 114.17, δ 107.63, δ 101.07, δ 55.59, δ 55.44.

HRMS (ESI-FT-ICR) m/z: [M+H]$^+$ calculated $C_{17}H_{17}O_4$ 285.11214 (monoisotopic mass), found 285.11213; [M+Na]$^+$ calculated $C_{17}H_{16}O_4Na$ 307.09408 (monoisotopic mass), found 307.09413.

2,4,4'-trimethoxychalcone (4)

yellow solid (12% yield); pf 87.2-88.2° C. $^1$H NMR (400 MHz, (CD$_3$)$_2$CO): δ 7.70 (H-2, H-6 and H-6', 3H, m), δ 7.62 (C$_β$H, 1H, d, J=15.6 Hz,), δ 7.53 (C$_α$H—CO, 1H, d, J=15.6 Hz), δ 7.03 (H-3 and H-5, 2H, m), δ 6.71 (H-3', 1H, d, J=2 Hz), δ 6.66 (H-5', 1H, dd, J=8 Hz and J=2 Hz); δ 3.99 (OCH$_3$, 3H, s); δ 3.93 (OCH$_3$, 3H, s); δ 3.89 (OCH$_3$3H, s). $^{13}$C NMR (100 MHz, (CD$_3$)$_2$CO): δ 189.08, δ 164.23, δ 161.45, δ 160.47, δ 140.87, δ 132.21, δ 131.73, δ 129.89, δ

128.13, δ 125.12, δ 122.33, δ 114.34, δ 113.22, δ 105.70, δ 98.34, δ 55.32, δ 55.06, δ 54.85.

HRMS (ESI-FT-ICR) m/z: [M+H]$^+$ calculated C$_{18}$H$_{19}$O$_4$ 299.12779 (monoisotopic mass), found 299.12822; [M+Na]$^+$ calculated C$_{18}$H$_{18}$O$_4$Na 321.10973 (monoisotopic mass), found 321.10938.

2'-hydroxy-4,4'-dimethoxy-3-(tetrahydropyran-2-yloxy)chalcone (5a)

yellow solid(35% yield); pf 123.9-125.9° C. $^1$H NMR (400 MHz, CDCl$_3$): δ 13.55 (OH, 1H, s), δ 7.83 (C$_\beta$H, 1H, d, J=15 Hz), δ 7.82 (H-6', 1H, d, J=8 Hz), δ 7.47 (H-2, 1H, d, J=2 Hz), δ 7.42 (C$_\alpha$H—CO, 1H, d, J=15.0 Hz), δ 7.28 (H-6, 1H, dd, J=8.4 Hz and J=1.6 Hz), δ 6.92 (H-5, 1H, d, J=8.4 Hz), δ 6.49-6.47 (H-3' and H-5', 2H, m), δ 5.47 (H-1", 1H, m), δ 4.01 (H$_\alpha$-5", 1H, m), δ 3.91 (OCH$_3$, 3H, s), δ 3.86 (OCH$_3$, 3H, s), δ 3.65 (H$_\beta$-5", 1H, m), δ 2.08-1.67 (H-2", H3" and H-4", 6H, m). $^{13}$C NMR (100 MHz, CDCl$_3$): δ 191.86, δ 166.64, δ 166.09, δ 148.94, δ 145.98, δ 144.34, δ 131.16, δ 128.51, δ 122.94, δ 118.48, δ 113.02, δ 110.61, δ 107.63, δ 101.11, δ 94.68, δ 62.94, δ 56.06, δ 55.58, δ 31.93, δ 30.89, δ 25.46, δ 19.76.

HRMS (ESI-FT-ICR) m/z: [M+H]$^+$ calculated for C$_{22}$H$_{25}$O$_6$ 385.16456 (monoisotopic mass), found 385.16486; [M+Na]$^+$ calculated C$_{22}$H$_{24}$O$_6$Na 407.14651 (monoisotopic mass), found 407.14568.

2', 3-dihydroxy-4,4'-dimethoxychalcone (5)

yellow solid (quantitative yield); pf 161.6-164.0° C. $^1$H NMR (400 MHz, DMSO-d$_6$): δ 13.63 (OH, 1H, s), δ 9.30 (OH, 1H, s) δ 8.29 (H-6', 1H, d, J=9.2 Hz), δ 7.82 (C$_\beta$H, 1H, d, J=15.2 Hz), δ 7.75 (C$_{\alpha H—CO}$, 1H, d, J=16 Hz), δ 7.41 (H-2, 1H, d, J=1.6 Hz), δ 7.36 (H-6, 1H, dd, J=8.4 Hz and J=1.6 Hz), δ 7.04 (H-5, 1H, d, J=8.4 Hz), δ 6.59 (H-5', 1H, dd, J=9.2 Hz and J=2.4 Hz), δ 6.54 (H-3', 1H, d, J=2.4 Hz), δ 3.88 (OCH$_3$, 6H, s). $^{13}$C NMR (100 MHz, DMSO-d6): δ 192.28, δ 166.26, δ 166.20, δ 151.02, δ 147.19, δ 145.22, δ 133.00, δ 128.01, δ 122.90, δ 118.88, δ 115.64, δ 114.40, δ 112.34, δ 107.72, δ 101.42, δ 56.19, δ 56.17.

HRMS (ESI-FT-ICR) m/z: [M+H]$^+$ calculated C$_{17}$H$_{17}$O$_5$ 301.10705 (monoisotopic mass), found 301.10709; [M+Na]$^+$ calculated 323.08899 C$_{17}$H$_{16}$O$_5$Na 323.08899 (monoisotopic mass), found 323.08861.

2'-hydroxy-3,4-dimethoxy-4'-(tetrahydropyran-2-yloxy)chalcone (6a)

yellow solid (18% yield); pf 116.3-118.6° C. $^1$H NMR (400 MHz, CDCl$_3$): δ 13.37 (OH, 1H, s), δ 7.85 (C$_\beta$H, 1H, d, J=15.2 Hz), δ 7.84 (H-6', 1H, d, J=9.2 Hz), δ 7.44 (C$_\alpha$H—CO, 1H, d, J=15.2 Hz), δ 7.25 (H-6, 1H, dd, J=8.4 Hz and J=1.6 Hz), δ 7.16 (H-2, 1H, d, J=1.6 Hz), δ 6.91 (H-5, 1H, d, J=8.4 Hz), δ 6.67 (H-3', 1H, d, J=2.4 Hz), δ 6.60 (H-5', 1H, dd, J=8.8 Hz and J=2.4 Hz), δ 5.51 (H-1", 1H, t), δ 3.96 (OCH$_3$, 3H, s), δ 3.94 (OCH$_3$, 3H, s), δ 3.89-3.83 (H$_\alpha$-5", 1H, m), δ 3.66-3.61 (H$_{62}$-5", 1H, m), δ 1.89-1.60 (H-2", H3" and H-4", 6H, m). $^{13}$C NMR (100 MHz, CDCl$_3$): δ 191.95, δ 166.21, δ 163.53, δ 151.60, δ 149.31, δ 144.64, δ 131.12, δ 127.82, δ 123.34, δ 118.10, δ 114.82, δ 111.19, δ 110.28, δ 108.45, δ 104.28, δ 96.17, δ 62.24, δ 56.03, δ 30.01, δ 25.00, δ 18.55.

HRMS (ESI-FT-ICR) m/z: [M+H] calculated C$_{22}$H$_{25}$O$_6$ 385.16456 (monoisotopic mass), found 385.16512; [M+Na] calculated C$_{22}$H$_{24}$O$_6$Na 407.14651 (monoisotopic mass), found 407.14554.

2'-hydroxy-3,4'-dimethoxy-4-(tetrahydropyran-2-yloxy)chalcone (7a)

yellow solid (20% yield); fp 90.5-93.0° C. $^1$H NMR (400 MHz, CDCl$_3$): δ 13.37 (OH, 1H, s), δ 7.84 (C$_\beta$H, 1H, d, J=15.2 Hz), δ 7.84 (H-6', 1H, d, J=9.2 Hz), δ 7.44 (C$_\alpha$H—CO, 1H, d, J=15.6 Hz), δ 7.23 (H-6, 1H, dd, J=8.4 Hz and J=1.6 Hz), δ 7.18-7.16 (H-2 and H-5, 2H, m), δ 6.50-6.48 (H-3' and H-5', 2H, m), δ 5.49 (H-1", 1H, m), δ 3.97 (H$_\alpha$-5", 1H, m), δ 3.94 (OCH$_3$, 3H, s), δ 3.86 (OCH$_3$, 3H, s), δ 3.63 (H$_\beta$-5", 1H, m), δ 2.05-1.57 (H-2", H3" and H-4", 6H, m). $^{13}$C NMR (100 MHz, CDCl$_3$): δ 191.81, δ 166.65, δ 166.06, δ 148.45, δ 146.83, δ 144.75, δ 131.11, δ 127.43, δ 123.49, δ 117.77, δ 114.94, δ 114.14, δ 110.20, δ 107.65, δ 101.6, δ 94.68, δ 56.05, δ 55.59, δ 30.70, δ 25.46, δ 19.76.

HRMS (ESI-FT-ICR) m/z: [M+H] calculated C$_{22}$H$_{25}$O$_6$ 385.16456 (monoisotopic mass), found 385.16469; [M+Na]$^+$ calculated C$_{22}$H$_{24}$O$_6$Na 407.14651 (monoisotopic mass), found 407.14616.

2', 4-dihydroxy-3,4'-dimethoxychalcone (7)

yellow solid (quantitative yield); pf 135.3-139.2° C. $^1$H NMR (400 MHz, (CD$_3$)$_2$CO): δ 13.58 (OH, 1H, s), δ 8.18 (OH, 1H, s), δ 8.00 (H-6', 1H, d, J=8.8 Hz), δ 7.73 (C$_\beta$H, 1H, d, J=15.2 Hz), δ 7.68 (C$_\alpha$H—CO, 1H, d, J=15.2 Hz), δ 7.41 (H-2, 1H, d, J=2 Hz), δ 7.21 (H-6, 1H, dd, J=1.6 Hz and J=8.4 Hz), δ 6.78 (H-5, 1H, d, J=8.4 Hz), δ 6.38 (H-5', 1H, dd, J=2.4 Hz and J=9.2 Hz), δ 6.33 (H-3', 1H, d, J=2.4 Hz), δ 3.81 (OCH$_3$, 3H, s), δ 3.76 (OCH$_3$, 3H, s). $^{13}$C NMR (100 MHz, (CD$_3$)$_2$CO): δ 192.16, δ 166.75, δ 166.26, δ 149.84, δ 147.95, δ 145.05, δ 131.84, δ 127.06, δ 124.20, δ 117.47, δ 115.35, δ 114.02, δ 111.22, δ 107.21, δ 100.80, δ 55.54, δ 55.20.

HRMS (ESI-FT-ICR) m/z: [M+H]$^+$ calculated C$_{17}$H$_{17}$O$_5$ 301.10705 (monoisotopic mass), found 301.10716; [M+Na] calculated C$_{17}$H$_{16}$O$_5$Na 323.08899 (monoisotopic mass), found 323.08904.

2'-hydroxy-4'-methoxy-4-(tetrahydropyran-2-yloxy)chalcone (8a)

yellow solid (quantitative yield); pf 120.8-123.4° C. $^1$H NMR (400 MHz, CDCl$_3$): δ 13.54 (OH, 1H, s) 7.87 (C$_\beta$H, 1H, d, J=15.6 Hz), δ 7.83 (H-6', 1H, d, J=10.4 Hz), δ 7.61-7.59 (H-2 and H-6, 2H, m), δ 7.47 (C$_\alpha$H—CO, 1H, d, J=15.6 Hz), δ 7.11-7.09 (H-3 and H-5, 2H, m), δ 6.50-6.48 (H-3' and H-5', 2H, m), δ 5.50 (H-1", 1H, m), δ 3.89 (H$_\alpha$-5", 1H, m), δ 3.87 (OCH$_3$, 3H, s), δ 3.63 (H$_\beta$-5", 1H, m), δ 2.03-1.67 (H-2", H3" and H-4", 6H, m). $^{13}$C NMR (100 MHz, CDCl$_3$): δ 191.93, δ 166.64, δ 166.07, δ 159.30, δ 144.32, δ 131.14, δ 130.57, δ 130.21, δ 128.24, δ 118.10, δ 116.79, δ 116.02, δ 114.18, δ 107.63, δ 101.09, δ 96.18, δ 62.06, δ 55.58, δ 30.17, δ 25.10, δ 18.57.

HRMS (ESI-FT-ICR) m/z: [M+H]$^+$ calculated for C$_{21}$H$_{23}$O$_5$ 355.15400 (monoisotopic mass), found 355.15443; [M+Na]$^+$ calculated for C$_{21}$H$_{22}$O$_5$Na 377.13594 (monoisotopic mass), found 377.13542.

2', 4-dihydroxy-4'-methoxychalcone (8)

yellow solid (resa70%); pf 152.8-158.5° C. $^1$H NMR (400 MHz, (CD$_3$)$_2$CO): δ 13.72 (OH, 1H, s), δ 9.08 (OH, 1H, s), δ 8.18 (H-6', 1H, d, J=8.8 Hz), δ 7.88 (C$_\beta$H, 1H, d, J=15.2 Hz), δ 7.80 (C$_{\alpha H—CO}$, 1H, d, J=15.6 Hz), δ 7.77 (H-2 and H-6, 2H, d, J=8.4 Hz), δ 6.95 (H-3 and H-5, 2H, dd, J=8.4 Hz), δ 6.55 (H-5', 1H, dd, J=2.4 Hz and J=9.2 Hz), δ 6.48 (H-3', 1H, d, J=2.4 Hz), δ 3.90 (OCH$_3$, 3H, s). $^{13}$C NMR (100 MHz, (CD$_3$)$_2$CO): δ 192.19, δ 166.72, δ 166.27, δ 160.20, δ 144.59, δ 131.87, δ 130.99, δ 126.67, δ 117.36, δ 115.91, δ 114.04, δ 107.17, δ 100.84, δ 55.17.

HRMS (ESI-FT-ICR) m/z: [M+H]$^+$ calculated C$_{16}$H$_{15}$O$_4$ 271.09649 (monoisotopic mass), found 271.09629; [M+Na]$^+$ calculated C$_{16}$H$_{14}$O$_4$Na 293.07843 (monoisotopic mass), found 293.07842.

2', 4-dihydroxy-4'-metoxydihydrochalcone (8b)

brown oil (yield 10%). $^1$H NMR (400 MHz, (CDCl$_3$): δ 12.81 (OH, 1H, s), δ 7.63 (H-6', 1H, d, J=9.6 Hz), δ 7.11 (H-3 and H-5, 2H, d, J=8.4 Hz), δ 6.77 (H-2 and H-6, 2H, d, J=8.4), δ 6.41 (H-3' and H-5', 2 H, m), δ 4.80 (OH, 1H, s), δ 3.83 (OCH₃, 3H, s), δ 3.20 (C$_\alpha$H₂—CO, 2H, t, J=8 Hz), δ 2.98 (C$_\beta$H₂, 2H, t, J=8 Hz). ¹³C NMR (100 MHz, (CDCl₃): δ 164.98, δ 164.36, δ 131.98, δ 130.46, δ 128.50, δ 114.35, δ 106.66, δ 99.91, δ 54.55, δ 38.92, δ 30.91, δ 28.68, δ 28.51, δ 21.68, δ 13.11, δ 0.00.

HRMS (ESI-FT-ICR) m/z: [M+H]⁺ calculated for C₁₆H₁₇O₄ 273.11214 (monoisotopic mass), found 273.11180; [M+Na]⁺ calculated C₁₆H₁₆O₄Na 295.09408 (monoisotopic mass), found 295.09452.

2'-hydroxy-4'-methoxychalcone (9)

yellow solid (yield 87%); pf 107.5-107.8° C. ¹H NMR (400 MHz, CDCl₃): δ 13.43 (OH, 1H, s), δ 7.89 (C$_\beta$H, 1H, d, J=15.6 Hz), δ 7.84 (H-6', 1H, d, J=8.4 Hz), δ 7.67-7.65 (H-2 and H-6, 2H, m), δ 7.65 (C$_{\alpha H-CO}$, 1H, d, J=15.6 Hz), δ 7.44-7.42 (H-3, H-4 and H-5, 3H, m), δ 6.51-6.48 (H-3' and H-5', 2H, m), δ 3.87 (OCH₃, 3H, s). ¹³C NMR (100 MHz, CDCl₃): δ 191.40, δ 166.27, δ 165.80, δ 143.95, δ 134.36, δ 130.78, δ 130.19, δ 128.53, δ 128.07, δ 119.90, δ 113.65, δ 107.31, δ 100.64, δ 55.14.

HRMS (ESI-FT-ICR) m/z: [M+H]⁺ calculated C₁₆H₁₅O₃ 255.10157 (monoisotopic mass), found 255.10180; [M+Na]⁺ calculated C₁₆H₁₄O₃Na 277.08352 (monoisotopic mass), found 277.08343.

2'-hydroxy-3,4'-dimethoxychalcone (10)

yellow solid (yield 35%); pf 89.2-91.8° C. ¹H NMR (400 MHz, (CD₃)₂CO): δ 13.56 (OH, 1H, s), δ 8.21 (H-6', 1H, d, J=8.8 Hz), δ 7.99 (C$_\beta$H, 1H, d, J=15.2 Hz,), δ 7.88 (C$_\alpha$H, 1H, d, J=15.6 Hz), δ 7.46-7.38 (H-2, H-4 and H-5, 3H, m), δ 7.05 (H-6, 1H, dd, J=8 Hz and J=2 Hz), δ 6.55 (H-5', 1H, dd, J=9.2 Hz and J=2.4 Hz), δ 6.50 (H-3', 1H, d, J=2.4 Hz), δ 3.91 (OCH₃, 3H, s); δ 3.89 (OCH₃, 3H, s). ¹³C NMR (100 MHz, (CD₃)₂CO): δ 192.16, δ 166.84, δ 166.57, δ 160.26, δ 144.24, δ 136.36, δ 132.17, δ 129.94, δ 121.58, δ 120.96, δ 116.68, δ 113.97, δ 113.40, δ 107.41, δ 100.83, δ 55.26, δ 54.84.

HRMS (ESI-FT-ICR) m/z: [M+H]⁺ calculated C₁₇H₁₇O₄ 285.11214 (monoisotopic mass), found 285.11230; [M+Na]⁺ calculated C₁₇H₁₆O₄Na 307.09408 (monoisotopic mass), found 307.09351.

2'-hydroxy-4'-methoxy-3-(tetrahydropyran-2-yloxy)chalcone (11a)

yellow solid (83.44% yield); pf 92.4-94.6° C. ¹H NMR (400 MHz, (CD₃)₂CO): δ 12.77 (OH, 1H, s), δ 7.45 (H-6', 1H, d, J=8.8 Hz) δ 7.20 (C$_\beta$H, 1H, d, J=15.6 Hz), δ 7.09 (C$_{\alpha H-CO}$, 1H, d, J=15.6 Hz), δ 6.76 (H-2, 1H, s), δ 6.70 (H-4, 1H, d, J=8 Hz), δ 6.62 (H-5, 1H, t, J=8 Hz), δ 6.4 (H-6, 1H, dd, J=2.4 Hz and J=8.4 Hz), δ 5.78 (H-5', 1H, dd, J=2.4 Hz and J=9.2 Hz), δ 5.72 (H-3', 1H, d, J=2.4 Hz), δ 4.79 (H-1'', 1H, t, J=3.2 Hz), δ 3.13 (OCH₃, 3H, s), δ 3.12-3.06 (H$_\alpha$-5'', 1H, m), δ 2.86-2.01 (H$_\beta$-5'', 1H, m), δ 1.22-0.82 (H-2'', H3'' and H-4'', 6H, m). ¹³C NMR (100 MHz, (CD₃)₂CO): δ 192.14, δ 166.83, δ 166.57, δ 157.65, δ 144.18, δ 136.24, δ 132.20, δ 129.88, δ 122.39, δ 120.94, δ 118.81, δ 116.38, δ 113.97, δ 107.43, δ 100.82, δ 96.07, δ 61.57, δ 55.26, δ 30.12, δ 25.04, δ 18.64.

HRMS (ESI-FT-ICR) m/z: [M+H]⁺ calculated C₂₁H₂₃O₅ 355.15400 (monoisotopic mass), found 355.15396; [M+Na]⁺ calculated C₂₁H₂₂O₅Na 377.13594 (monoisotopic mass), found 377.13506.

2',4-dihydroxy-4'-methoxychalcone (11)

yellow solid (resa 10.7%); pf 174.6-177.8° C. ¹H NMR (400 MHz, (CD₃)₂CO): δ 12.71 (OH, 1H, s), δ 7.82 (OH, 1H, s), δ 7.38 (H-6', 1H, d, J=8.8 Hz) δ 7.08 (C$_\beta$H, 1H, d, J=15.6 Hz), δ 7.00 (C$_{\alpha H-CO}$, 1H, d, J=15.6 Hz), δ 6.49 (H-2, H-4, H-5; 3H, m), δ 6.13 (H-6, 1H, dd, J=2 Hz and J=7.6 Hz), δ 5.73 (H-5', 1H, dd, J=2.4 Hz and J=9.2 Hz), δ 5.65 (H-3', 1H, d, J=2.4 Hz) δ 3.07 (OCH₃, 3H, s). ¹³C NMR (100 MHz, (CD₃)₂CO): δ 192.18, δ 166.80, δ 166.54, δ 157.88, δ 144.38, δ 136.37, δ 132.15, δ 129.98, δ 120.69, δ 120.33, δ 117.87, δ 115.27, δ 113.97, δ 107.39, δ 100.84, δ 55.26.

HRMS (ESI-FT-ICR) m/z: [M+H]⁺ calculated C₁₆H₁₅O₄ 271.09649 (monoisotopic mass), found 271.09660; [M+Na]⁺ calculated C₁₆H₁₄O₄Na 293.07843 (monoisotopic mass), found 293.07868.

2,2'-dihydroxy-4'-methoxychalcone (12)

yellow solid (yield 4%); pf 159.9-164.0° C. ¹H NMR (400 MHz, (CD₃)₂CO): δ 13.70 (OH, 1H, s), δ 9.30 (OH, 1H, s), δ 8.33 (C$_\beta$H, 1H, d, J=15.6 Hz), δ 8.17 (H-6', 1H, d, J=9.2 Hz), δ 8.03 (C$_{\alpha H-CO}$, 1H, d, J=15.6 Hz), δ 7.89 (H-6, 1H, dd, J=1.6 Hz and J=8.4 Hz), δ 7.36-7.32 (H-4, 1H, m), δ 7.05 (H-3, 1H, dd, J=2.8 Hz and J=8 Hz), δ 6.98 (H-5, 1H, t, J=7.6 Hz), δ 6.59 (H-5', 1H, dd, J=2.4 Hz and J=8.8 Hz,), δ 6.52 (H-3', 1H, d, J=2.4 Hz), δ 3.93 (OCH₃, 3H, s). ¹³C NMR (100 MHz, (CD₃)₂CO): δ 193.73, δ 192.54, δ 166.77, δ 166.35, δ 157.20, δ 148.05, δ 139.83, δ 131.96, δ 129.16, δ 121.94, δ 120.03, δ 116.27, δ 114.07, δ 107.29, δ 100.86, δ 55.22.

HRMS (ESI-FT-ICR) m/z: [M+H]⁺ calculated C₁₆H₁₅O₄ 271.09649 (monoisotopic mass), found 271.09631; [M+Na]⁺ calculated C₁₆H₁₄O₄Na 293.07843 (monoisotopic mass), found 293.07863.

2'-hydroxy-2,4'-dimethoxychalcone (13)

yellow solid (yield 46%); pf 74.7-77.9° C. ¹H NMR (400 MHz, (CD₃)₂CO): δ 12.87 (OH, 1H, s), δ 7.51 (C$_\beta$H, 1H, d, J=15.6 Hz), δ 7.40 (H-6', 1H, d, J=8.8 Hz), δ 7.21 (C$_\alpha$H—CO, 1H, d, J=15.6 Hz), δ 7.16 (H-6, 1H, dd, J=7.6 Hz and J=0.8 Hz), δ 6.70 (H-4, 1H, td, J=1.2 Hz and J=8.0 Hz), δ 6.37 (H-3, 1H, d, J=8.4 Hz), δ 6.28 (H-5, 1H, d, J=7.6 Hz), δ 5.78 (H-5', 1H, dd, J=2.4 Hz and J=9.2 Hz), δ 5.72 (H-3', 1H, d, J=2.4 Hz), δ 3.22 (OCH₃, 3H, s), δ 3.14 (OCH₃, 3H, s). ¹³C NMR (100 MHz, (CD₃)₂CO): δ 192.44, δ 166.80, δ 166.42, δ 158.93, δ 139.26, δ 132.30, δ 131.99, δ 128.88, δ 123.48, δ 120.72, δ 120.59, δ 114.04, δ 111.56, δ 107.34, δ 100.85, δ 55.24, δ 54.64.

HRMS (ESI-FT-ICR) m/z: [M+H]⁺ calculated C₁₇H₁₇O₄ 285.11214 (monoisotopic mass), found 285.11237; [M+Na]⁺ calculated C₁₇H₁₆O₄Na 307.09408 (monoisotopic mass), found 307.09351.

2'-hydroxy-4-(tetrahydropyran-2-yloxy)chalcone (14a)

yellow solid (64% yield); pf 138.6-139.0° C. ¹H NMR (400 MHz, (CD₃)₂CO): δ 12.24 (OH, 1H, s), δ 7.47 (H-6', 1H, d, J=7.6 Hz), δ 7.16 (C$_\beta$H, 1H, d, J=15.6 Hz), δ 7.12 (C$_\alpha$H—CO, 1H, d, J=15.6 Hz) δ 7.06 (H-2 and H-6, 2H, d, J=8.8 Hz), δ 6.76 (H-4', 1H, t, J=8 Hz), δ 6.34 (H-3 and H-5, 2H, d, J=8.4 Hz), δ 6.21-6.17 (H-3' and H-5', 2H, m), δ 4.77 (H-1'', 1H, t, J=3.2 Hz), δ 3.05-2.99 (H$_{60}$-5'', 1H, m), δ 32.83-2.74 (H$_\beta$-5'', 1H, m), δ 1.16-0.78 (H-2'', H3'' and H-4'', 6H, m). ¹³C NMR (100 MHz, (CD₃)₂CO): δ 194.04, δ 163.64, δ 159.70, δ 145.34, δ 136.34, δ 130.80, δ 130.35, δ 128.14, δ 120.05, δ 118.86, δ 118.17, δ 116.74, δ 107.43, δ 95.97, δ 61.63, δ 56.84, δ 29.97, δ 24.95, δ 18.51, δ 18.01.

HRMS (ESI-FT-ICR) m/z: [M+H]⁺ calculated C₂₀H₂₁O₄ 325.14344 (monoisotopic mass), found 325.14319; [M+Na]⁺ calculated C₂₀H₂₀O₄Na 347.12538 (monoisotopic mass), found 347.12539.

2',4-dihydroxychalcone (14)

yellow solid (60% yield); pf 148.8-150.2° C. ¹H NMR (400 MHz, (CD₃)₂CO): δ 12.15 (OH, 1H, s), δ 8.17 (OH, 1H, s), δ 7.31 (H-6', 1H, d, J=7.2 Hz) δ 6.98 (C$_\beta$H, 1H, d, J=15.6 Hz), δ 6.93 (C$_\alpha$H—CO, 1H, d, J=15.2 Hz), δ 6.85 (H-2 and H-6, 2H, d, J=8.8 Hz), δ 6.60 (H-4', 1H, t, J=7.2 Hz), δ 6.05-5.99 (H-3, H-3', H-5 and H-5', 4H, m). ¹³C NMR (100 MHz, (CD₃)₂CO): δ 194.02, δ 163.62, δ 160.51, δ

145.79, δ 136.21, δ 131.28, δ 130.26, δ 126.50, δ 120.09, δ 118.81, δ 118.03, δ 117.10, δ 115.99.

HRMS (ESI-FT-ICR) m/z: [M+H]$^+$ calculated $C_{15}H_{13}O_3$ 241.08592 (monoisotopic mass), found 241.08620; [M+Na]$^+$ calculated $C_{15}H_{12}O_3Na$ 263.06787 (monoisotopic mass), found 263.06769.

2'-methoxy-4-(tetrahydropyran-2-yloxy)chalcone (15a)

yellow solid (yield 38%); pf 83.7-89.3° C. $^1$H NMR (400 MHz, (CD$_3$)$_2$CO): δ 6.88 (H-2 and H-6, 2H, d, J=8.4 Hz), δ 6.78-6.72 (C$_\beta$H, H-4' and H-6', 3H, m), δ 6.57 (C$_{\alpha H—CO}$, 1H, d, J=16 Hz), δ 6.38 (H-3', 1H, d, J=8 Hz), δ 6.32 (H-3 and H-5, 2H, d, J=8.8 Hz), δ 6.27 (H-5', 1H, d, J=7.2 Hz), δ 4.75 (H-1", 1H, t, J=3.2 Hz), δ 3.14 (OCH$_3$, 3H, s), δ 3.06-3.01 (H$_\alpha$-5", 1H, m), δ 2.83-2.78 (H$_\beta$-5", 1H, m), δ 1.28-0.79 (H-2", H3" and H-4", 6H, m). $^{13}$C NMR (100 MHz, (CD$_3$)$_2$CO): δ 191.69, δ 159.05, δ 158.15, δ 142.08, δ 132.63, δ 129.91, δ 129.81, δ 129.75, δ 128.52, δ 125.24, δ 120.52, δ 116.72, δ 111.94, δ 96.01, δ 61.63, δ 55.28, δ 30.02, δ 24.98, δ 18.57.

HRMS (ESI-FT-ICR) m/z: [M+H]$^+$ calculated $C_{21}H_{23}O_4$ 339.15909 (monoisotopic mass), found 339.15784; [M+Na]$^+$ calculated $C_{21}H_{22}O_4Na$ 361.14103 (monoisotopic mass), found 361.14116.

4-hydroxy-2'-methoxychalcone (15)

yellow solid(82% yield); pf 135.3-138.0° C. $^1$H NMR (400 MHz, (CD$_3$)$_2$CO): δ 8.05 (OH, 1H, s), δ 6.66 (H-2 and H-6, 2H, d, J=8.8 Hz), δ 6.61-6.57 (C$_\beta$H, H-4' and H-6', 3H, m), δ 6.36 (C$_\alpha$H—CO, 1H, d, J=16 Hz), δ 6.23 (H-3', 1H, d, J=8 Hz), δ 6.12 (H-5', 1H, t, J=7.6 Hz), δ 5.99 (H-3 and H-5, 2H, d, J=8.4 Hz), δ 2.99 (OCH$_3$, 3H, s). $^{13}$C NMR (100 MHz, (CD$_3$)$_2$CO): δ 191.81, δ 159.78, δ 158.07, δ 142.66, δ 132.48, δ 130.34, δ 129.88, δ 129.74, δ 126.77, δ 124.30, δ 120.49, δ 115.90, δ 111.92, δ 55.26.

HRMS (ESI-FT-ICR) m/z: [M+H]$^+$ calculated $C_{16}H_{15}O_3$ 255.10157 (monoisotopic mass), found 255.10180; [M+Na]$^+$ calculated $C_{16}H_{14}O_3Na$ 277.08352 (monoisotopic mass), found 277.08348.

2', 4'-dimethoxy-4-(tetrahydropyran-2-yloxy)chalcone (16a)

yellow solid (15% yield); pf 134.7-135.9° C. $^1$H NMR (400 MHz, CDCl$_3$): δ 7.73 (H-6', 1H, d, J=8 Hz), δ 7.64 (C$_\beta$H, 1H, d, J=16 Hz), δ 7.53 (H-2 and H-6, 2H, d, J=8.8 Hz), δ 7.38 (C$_\alpha$H—CO, 1H, d, J=16 Hz), δ 7.05 (H-3 and H-5, 2H, d, J=8.8 Hz), δ 6.56 (H-5', 1H, dd, J=2—J=8 Hz), δ 6.49 (H-3', 1H, d, J=2.4 Hz), δ 5.47 (H-1", 1H, t, J=2.8 Hz), δ 3.90-3.87 (H$_\alpha$-5", OCH$_3$, 7H, m), δ 3.61 (H$_\beta$-5", 1H, m), δ 2.03-1.59 (H-2", H-3" and H-4", 6H, m). $^{13}$C NMR (100 MHz, CDCl$_3$): δ 190.75, δ 163.98, δ 160.28, δ 158.71, δ 142.14, δ 132.76, δ 129.87, δ 128.90, δ 125.26, δ 122.49, δ 116.65, δ 105.10, δ 98.70, δ 96.18, δ 62.07, δ 55.77, δ 55.55, δ 30.22, δ 25.13, δ 18.64.

HRMS (ESI-FT-ICR) m/z: [M+H]$^+$ calculated $C_{22}H_{25}O_5$ 369.16965 (monoisotopic mass), found 369.16998; [M+Na]$^+$ calculated $C_{22}H_{24}O_5Na$ 391.15159 (monoisotopic mass), found 391.15055.

4-hydroxy-2', 4'-dimethoxychalcone (16)

yellow solid (yield 92%); pf 139.9-142.2° C. $^1$H NMR (400 MHz, CDCl$_3$): δ 12.87 (OH, 1H, s), δ 7.51 (C$_\beta$H, 1H, d, J=15.6 Hz), δ 7.40 (H-6', 1H, d, J=8.8 Hz), δ 7.21 (C$_\alpha$H—CO, 1H, d, J=15.6 Hz), δ 7.16 (H-6, 1H, dd, J=7.6 Hz, J=0.8 Hz), δ 6.70 (H-4, 1H, td, J=8.0 Hz, J=1.2 Hz), δ 6.37 (H-3, 1H, d, J=8.4 Hz), δ 6.28 (H-5, 1H, d, J=7.6 Hz), δ 5.78 (H-5', 1H, dd, J=9.2 Hz, J=2.4 Hz), δ 5.72 (H-3', 1H, d, J=2.4 Hz), δ 3.22 (OCH$_3$, 3H, s), δ 3.14 (OCH$_3$, 3H, s). $^{13}$C NMR (100 MHz, CDCl$_3$): δ 191.31, δ 164.13, δ 160.38, δ 158.10, δ 142.81, δ 132.80, δ 130.32, δ 127.89, δ 124.68, δ 122.29, δ 115.98, δ 105.14, δ 98.75, δ 55.77, δ 55.57.

HRMS (ESI-FT-ICR) m/z: [M+H]$^+$ calculated $C_{17}H_{17}O_4$ 285.11214 (monoisotopic mass), found 285.11192; [M+Na]$^+$ calculated $C_{17}H_{16}O_4Na$ 307.09408 (monoisotopic mass), found 307.09369.

4'-methoxy-4-(tetrahydropyran-2-yloxy)chalcone (17a)

yellow solid (yield 66%); pf 134.7-135.9° C. $^1$H NMR (400 MHz, (CDCl$_3$): δ 8.03 (H-2 and H-6, 2H, d, J=8.8 Hz), δ 7.78 (C$_\beta$H, 1H, d, J=15.6 Hz), δ 7.58 (H-2' and H-6', 2H, d, J=8.8 Hz), δ 7.43 (C$_{\alpha H—CO,}$ 1H, d, J=15.6 Hz), δ 7.08 (H-3 and H-5, 2H, d, J=8.4 Hz), δ 6.99 (H-3' and H-5', 2H, d, J=8.4 Hz), δ 5.48 (H-1", 1H, t, J=2.8 Hz), δ 3.91-3.85 (H$_\alpha$-5", 1H, m), δ 3.89 (OCH$_3$, 3H, s), δ 3.65-3.60 (H$_\beta$-5", 1H, m), δ 2.02-1.60 (H-2", H-3" and H-4", 6H, m). $^{13}$C NMR (100 MHz, CDCl$_3$): δ 188.84, δ 163.29, δ 159.00, δ 143.88, δ 131.37, δ 130.73, δ 129.98 δ 128.53, δ 119.81, δ 116.72, δ 113.80, δ 96.17, δ 62.06, δ 55.50, δ 30.20, δ 25.13, δ 18.61.

HRMS (ESI-FT-ICR) m/z: [M+H]$^+$ calculated $C_{21}H_{23}O_4$ 339.15909 (monoisotopic mass), found 339.15756; [M+Na]$^+$ calculated $C_{21}H_{22}O_4Na$ 361.14103 (monoisotopic mass), found 361.14116.

4-hydroxy-4'-methoxychalcone (17).

yellow solid (yield 96%); pf 171.3-175.8° C. $^1$H NMR (400 MHz, (CD$_3$)$_2$CO): δ 8.17 (H-2 and H-6, 2H, d, J=8.8 Hz), δ 7.77 (C$_\beta$H, 1H, d, J=15.6 Hz), δ 7.79-7.71 (H-2' and H-6', 2H, m), δ 7.73 (C$_\alpha$H—CO, 1H, d, J=16 Hz), δ 7.10 (H-3' and H-5', 2H, d, J=8.8 Hz), δ 6.96 (H-3 and H-5, 2H, d, J=8.8 Hz), δ 3.94 (OCH$_3$, 3H, s). $^{13}$C NMR (100 MHz, (CD$_3$)$_2$CO): δ 187.24, δ 163.39, δ 159.86, δ 143.40, δ 131.43, δ 130.55, δ 130.51, δ 126.88, δ 118.71, δ 115.86, δ 113.75, δ 55.03.

HRMS (ESI-FT-ICR) m/z: [M+H]$^+$ calculated $C_{16}H_{15}O_3$ 255.10157 (monoisotopic mass), found 255.10177; [M+Na]$^+$ calculated $C_{16}H_{14}O_3Na$ 277.08352 (monoisotopic mass), found 277.08332.

Chromatographic Conditions for Determining the Purity

Analytical purification by means of HPLC was carried out with a Waters 2690 Separation Module, equipped with a 20-μl Rheodyne Model 8125 Injector and a Multi-Wavelength Programmable Model M486 Detector (PDA). Empower Chromatography Manager Software was used for data analysis. The purity, determined by HPLC, of the compounds subjected to biological tests was greater than 95%.

Compound A, Column: Phenomenex Luna C18, 5.0 μm (150×4.6 mm). Eluent A) aqueous solution of trifluoroacetic acid 0.03% (v/v). Eluent B) acetonitrile. Elution gradient: for 1 minute 80% A and 20% B; 1 to 10 minutes 60% A and 40% B; from 10 to 20 minutes 100% of B; 20 to 25 minutes 80% A and 20% B. Flow: 1.0 ml/min. Detector: UV lamp at wavelength 290 nm. Retention time ($R_t$)=7.90 min.

Compound B, Column: Phenomenex Luna C18, 5.0 μm (250×4.6 mm). Eluent A) water/acetonitrile=95: 5 (v/v). Eluent B) water/acetonitrile=5:95 (v/v). Elution gradient: for 5 minutes A:B=50:50; from 5 to 20 minutes up to 100% of B; from 20 to 25 minutes 100% of B. Flow: 1.0 ml/min. Detector: UV lamp at wavelength 295 nm. Retention time ($R_t$)=13.12 min.

Compound E, Column: Phenomenex Luna C18, 5.0 μm (250×4.6 mm). Eluent A) methanol. Eluent B) water. Elution gradient: for 6 minutes A:B=65:35; from 6 to 8 minutes up to 81% of A; from 8 to 15 minutes A:B=81:19; from 15 to 20 minutes up to 65% of A. Flow: 1.0 ml/min. Detector: UV lamp at wavelength 325 nm.

Retention time ($R_t$)=5.02 min.

Compound F, Column: Phenomenex Luna C18, 5.0 μm (250×4.6 mm). Eluent: methanol/water (90:10, v/v). Flow: 1.0 ml/min. Detector: UV lamp at wavelength 237 nm. Retention time $(R_t)$=5.83 min.

For compounds 1-17, HPLC analytical separations were performed using a Luna C18 stainless steel column, 5 μm (250×4.6 mm internal diameter, purchased from Phenomenex Inc.) Eluent A) water/acetonitrile (95:5, v/v). Eluent B) water/acetonitrile=5:95 (v/v). Elution gradient: for 5 minutes A:B=50:50; for 15 minutes up to 100% of B; for 5 minutes 100% of B. Flow: 1.0 ml/min. Detector: UV lamp at wavelength 200-400 nm.

Compound 1, 95.01% $R_t$=11.88 min (at 295 nm); compound 2, 98.41% $R_t$=15.67 min (at 295 nm); compound 3, 98.92 $R_t$=17.98 min (at 295 nm); compound 4, 99.29% $R_t$=14.76 min (at 295 nm); compound 5a, 98.28% $R_t$=19.44 min (at 295 nm); compound 5, 99.76% $R_t$=13.39 min (at 295 nm); compound 6a, 100% $R_t$=19.45 min (at 295 nm); compound 7a, 99.85% $R_t$=19.26 min (at 295 nm); compound 7, 99.36% $R_t$=12.98 min (at 295 nm); compound 8a, 99.98% $R_t$=20.95 min (at 295 nm); compound 8, 98.87% $R_t$=12.61 min (at 295 nm); compound 8b, 97.40% $R_t$=11.94 min (at 295 nm); compound 9, 100% $R_t$=18.30 min (at 295 nm); compound 10, 99.29% $R_t$=18.12 min (at 295 nm); compound 11a, 100.00% $R_t$=21.01 min (at 295 nm); compound 11, 96.25% $R_t$=13.15 min (at 295 nm); compound 12, 95.24% $R_t$=13.15 min (at 295 nm); compound 13, 99.41% $R_t$=18.78 min (at 295 nm); compound 14a, 98.68% $R_t$=21.01 min (at 295 nm); compound 14, 99.31% $R_t$=12.77 min (at 295 nm); compound 15a, 98.84% $R_t$=18.43 min (at 295 nm); compound 15, 95.57% $R_t$=8.67 min (at 295 nm); compound 16a, 100.00% $R_t$=17.83 min (at 295 nm); compound 16, 99.53% $R_t$=8.18 min (at 295 nm); compound 17a, 95.00% $R_t$=17.41 min (at 295 nm); compound 17, 98.40% $R_t$=8.93 min (at 295 nm).

Cell Lines and Treatments

The cell lines DND41 (ACC 525, DSMZ, Braunschweig, GERMANY), KOPTK1 (RRID: CVCL_4965) were maintained in culture in RPMI-1640 (Gibco, Carlsbad, Calif., USA) with 10% fetal bovine serum. TALL-1 cells (ACC-521: DSMZ, Braunschweig, GERMANY) were cultured in RPMI-1640 (Gibco, Carlsbad, Calif., USA) supplemented with 20% fetal bovine serum, while HaCaT cells (ACC-771: DSMZ, Braunschweig, GERMANY) were maintained in Eagle's culture medium according to Dulbecco (Gibco, Carlsbad, Calif., USA) containing 10% fetal bovine serum. Cells were treated with the naturally-occurring compounds A-H or with compounds 1-17 for times and concentrations indicated in the text.

Proliferation Analysis and Calculation of $IG_{50}$

Cells were seeded in 96-well plates with a density of $5 \times 10^5$ cells/ml ($5 \times 10^4$ cells per well) and treated for the times and the concentrations of the various compounds, as indicated in the text.

All treatments were carried out in triplicate, including control treatments. All treatment reactions contained a final concentration of 1% DMSO (D5879; Sigma-Aldrich, St Louis, Mo., USA). To quantify vitality, cells were assayed by the MTS CellTiter 96® AQueous One Solution Cell Proliferation Assay (G3580; Promega, Madison, Wis., USA). Absorbance was detected at 490 nm using the Glo-Max Multidetection System instrument (Promega, Madison, Wis., USA). Data were collected in the form of absorbance units (ABSs) and standardized to obtain the proliferation rate (MTS) through the equation:

% cell proliferation=$(ABS_{cell\ culture+compound} - ABS_{culture\ medium+compound})/(ABS_{cell\ culture+DMSO} - ABS_{culture\ medium+DMSO}) \times 100$.

The 50% inhibition concentration was calculated using the GraphPad Prism software program (GraphPad Software Inc., La Jolla, Calif., USA).

Protein Extraction, Immunoblotting, Antibodies

Laemmli Sample Buffer (161-0737; Bio-Rad Laboratories Inc., Hercules, Calif., USA) was added to each cell pellet. Cells were lysed by ultrasonic sonication and to each mixture 5% 2-mercaptoethanol (161-0710; Bio-Rad Laboratories Inc., Hercules, Calif., USA) was added. Samples were denatured at 100° C. for 5 min and protein mixtures were separated by means of Sodium Dodecyl Sulphate-Polyacrylamide Gel Electrophoresis using 8% acrylamide and transferred onto nitrocellulose membranes. After transfer, the membranes pre-saturated in 5% Blot Dry Fat Milk (1706404; Bio-Rad Laboratories Inc., Hercules, Calif., USA) were incubated for 16 hours at +4° C. with the following primary antibodies diluted at 1:1000 in 5% Dry Fat Milk (1706404; Bio-Rad Laboratories Inc., Hercules, Calif., USA): Notch1Val1744 (2421; Cell Signaling Technology, Beverly, Mass., USA), Notch3 (2889; Cell Signaling Technology, Beverly, Mass., USA) and β-actin (sc-47778; Santa Cruz Biotechnology, Santa Cruz, Calif., USA). Subsequently, filters were incubated for 1 hour at room temperature with the following secondary antibodies: anti-rabbit (sc-2004, Santa Cruz Biotechnology, Santa Cruz, Calif., USA) or anti-mouse (sc-2005, Santa Cruz Biotechnology, Santa Cruz, Calif., USA). Chemiluminescence signal detection was performed using the ECL Advanced Detection System substrate (RPN2135; E Healthcare UK Limited, Buckinghamshire, UK).

Total RNA Isolation and Real-Time PCR

Total RNA from the cell pellets was extracted using TRIzol reagent (15596018, Invitrogen, Carlsbad, Calif., USA) following the manufacturer's instructions. From 100 ng to 2 μg of total RNA per sample was retroscribed using the High Capacity cDNA Reverse Transcription Kit (4368814; Applied Biosystems, Foster City, Calif., USA) and following the manufacturer's instructions. Real-time PCR experiments were performed using ViiA™ 7 Real-Time PCR System (Applied Biosystems, Foster City, Calif., USA). Taqman Gene Expression Master Mix and Taqman Gene Expression Assays for HES1 (Hs00172878_m1), cMYC (Hs00905030_m1), DELTEX1 (Hs01092201_m1) and GAPDH (Hs02758991_g1) were provided by Applied Biosystems, Foster City, Calif., USA. The results were analyzed using the ΔΔCt method, normalizing the obtained values with respect to those obtained for GAPDH.

REFERENCES

Chokchaisiri, R., Suaisom, C., Sriphota, S., Chindaduang, A., Chuprajob, T., and Suksamrarn, A. (2009). Bioactive flavonoids of the flowers of Butea monosperma. Chemical & pharmaceutical bulletin 57, 428-432.

Compagnone, R., and Rodriguez, M. C. (1993). Coumarins from Pilocarpus racemosus. Fitoterapia 64, 557.

Cuca L E, M. J., and Delle Monache, F. (1998). Constituyentes quimicos de Zanthoxylum monophyllum. Revista Colombiana de Quimica 27, 17-27.

Delle Monache, F., Marquina Mac-Quhae, M., Delle Monache, G., Marini-Bettolo, G. B., and Alves De Lima, A. (1983). Xanthones, xanthonolignoids and other constituents of the roots of vismia guaramirangae. Phytochemistry 22, 227-232.

Delle Monache, G., De Mello, J. F., Delle Monache, F., Marini-Bettolo, G. B., De Lima, O. G., and De Barros Coelho, J. S. (1974). New prenylated flavonoids of Cordoa piaca (Lonchocarpus sp.). Gazz Chim Ital 104, 861-865.

Dong, Y., Zhang, T., Li, J., Deng, H., Song, Y., Zhai, D., Peng, Y., Lu, X., Liu, M., Zhao, Y., et al. (2014). Oridonin inhibits tumor growth and metastasis through anti-angiogenesis by blocking the Notch signaling. PloS one 9, e113830.

Koduru, S., Kumar, R., Srinivasan, S., Evers, M. B., and Damodaran, C. (2010). Notch-1 inhibition by Withaferin-A: a therapeutic target against colon carcinogenesis. Molecular cancer therapeutics 9, 202-210.

Kunnimalaiyaan, S., Sokolowski, K. M., Balamurugan, M., Gamblin, T. C., and Kunnimalaiyaan, M. (2015). Xanthohumol inhibits Notch signaling and induces apoptosis in hepatocellular carcinoma. PloS one 10, e0127464.

Rashid, M. A., Gray, A. I., and Waterman, P. G. (1995). Myrtenyl acetate from Phebalium tuberculosum ssp. megaphyllum. Fitoterapia 66, 473.

Raymond, J. W., Gardiner, E. J., and Willett, P. (2002). Heuristics for similarity searching of chemical graphs using a maximum common edge subgraph approach. Journal of chemical information and computer sciences 42, 305-316.

Schweigert, N., Zehnder, A. J., and Eggen, R. I. (2001). Chemical properties of catechols and their molecular modes of toxic action in cells, from microorganisms to mammals. Environmental microbiology 3, 81-91.

Sogawa, S., Nihro, Y., Ueda, H., Miki, T., Matsumoto, H., and Satoh, T. (1994). Protective effects of hydroxychalcones on free radical-induced cell damage. Biological & pharmaceutical bulletin 17, 251-256.

Stahl, M., and Mauser, H. (2005). Database clustering with a combination of fingerprint and maximum common substructure methods. Journal of chemical information and modeling 45, 542-548.

Studzinska-Sroka, E., Holderna-Kedzia, E., Galanty, A., Bylka, W., Kacprzak, K., and Cwiklinska, K. (2015). In vitro antimicrobial activity of extracts and compounds isolated from Cladonia uncialis. Natural product research 29, 2302-2307.

Yang, Y. N., Zhu, H., Chen, Z., Liu, F., An, Y. W., Feng, Z. M., Jiang, J. S., and Zhang, P. C. (2015). NMR spectroscopic method for the assignment of 3,5-dioxygenated aromatic rings in natural products. Journal of natural products 78, 705-711.

Zhong, L., Zhou, L., Zhou, Y., Chen, Y., Sui, P., Wang, J., and Wang, M. (2012). Antimicrobial flavonoids from the twigs of Populus nigra x Populus deltoides. Natural product research 26, 307-313.

The invention claimed is:

1. A method of treating T-cell acute lymphoblastic leukemia (T-ALL) in a subject, comprising administering to the subject a compound of formula (I), the compound of formula (I) being an inhibitor of Notch signaling, (I)

wherein
X and Y are carbon atoms bound by a single or double bond having, independently, an E or Z configuration;
$R_{1'}$ is hydrogen, halogen, $OR_A$, $C(=O)R_A$, $C(=O)OR_A$, $OC(=O)R_A$, $SR_A$, $SO_2R_A$, $SO_3R_A$, $OSO_2R_A$, $OSO_3R_A$, $N(R_A)_2$, $NHC(=O)R_A$, $C(=O)N(R_A)_2$, or $C(R_A)_3$;
$R_{2'}$, $R_{3'}$, $R_1$, $R_2$, $R_3$ are the same or different and independently selected from: hydrogen; halogen; $OR_B$; $C(=O)R_B$; $C(=O)OR_B$; $OC(=O)R_B$; $SR_B$; $SO_2R_B$; $SO_3R_B$; $OSO_2R_B$; $OSO_3R_B$; $N(R_B)_2$; $NHC(=O)R_B$; $C(=O)N(R_B)_2$; $C(R_B)_3$; a linear or branched, saturated or unsaturated $C_{1-7}$ acyclic aliphatic group optionally containing up to three heteroatoms independently selected from nitrogen, oxygen or sulfur; a $C_{5-7}$ cycloalkyl group; a phenyl; a $C_{5-7}$ heterocyclic group;
wherein at each occurrence RA and RB are independently selected from: hydrogen; a linear or branched, saturated or unsaturated $C_{1-7}$ aliphatic group optionally containing up to three heteroatoms independently selected from nitrogen, oxygen or sulfur; a $C_{5-7}$ cycloalkyl group; a phenyl group; a $C_{5-7}$ heterocyclic group;
and pharmaceutically acceptable salts thereof,
wherein the compound is selected from:
2',3,4,4'-tetramethoxychalcone (1);
2'-hydroxy-3,4,4'-trimethoxychalcone (2);
2'-hydroxy-4,4'-dimethoxychalcone (3);
2',4,4'-trimethoxychalcone (4);
2',3-dihydroxy-4,4'-dimethoxychalcone (5);
2'-hydroxy-3,4'-dimethoxy-4-(tetrahydropyran-2-yloxy)chalcone (7a);
2',4-dihydroxy-3,4'-dimethoxychalcone (7);
2'-hydroxy-4'-methoxy-4-(tetrahydropyran-2-yloxy)chalcone (8a);
2',4-dihydroxy-4'-methoxychalcone (8);
2'-hydroxy-4'-methoxychalcone (9);
2'-hydroxy-3,4'-dimethoxychalcone (10);
2'-hydroxy-4'-methoxy-3-(tetrahydropyran-2-yloxy)chalcone (11a);
2',3-dihydroxy-4'-methoxychalcone (11);
2,2'-dihydroxy-4'-methoxychalcone (12);
2'-hydroxy-2,4'-dimethoxychalcone (13);
2'-hydroxy-4-(tetrahydropyran-2-yloxy)chalcone (14a);
2'-methoxy-4-(tetrahydropyran-2-yloxy)chalcone (15a);
4-hydroxy-2'-methoxychalcone (15);
2',4'-dimethoxy-4-(tetrahydropyran-2-yloxy)chalcone (16a);
4-hydroxy-2',4'-dimethoxychalcone (16);
4'-methoxy-4-(tetrahydropyran-2-yloxy)chalcone (17a); and
4-hydroxy-4'-methoxychalcone (17).

2. The method according to claim 1, wherein X and Y are carbon atoms bound by a double bond having, independently, an E or Z configuration.

3. A method of treating T-cell acute lymphoblastic leukemia (T-ALL) in a subject, comprising administering to the subject a compound of formula (I), the compound of formula (I) being an inhibitor of Notch signaling, (I)

wherein

X and Y are carbon atoms bound by a single or double bond having, independently, an E or Z configuration;

$R_{1'}$ is hydrogen, halogen, $OR_A$, $OC(=O)R_A$, $SR_A$, $SO_2R_A$, $SO_3R_A$, $OSO_2R_A$, $OSO_3R_A$, $C(R_A)_3$;

$R_{2'}$, $R_{3'}$, $R_1$, $R_2$, $R_3$ are the same or different and independently selected from: a linear or branched, saturated or unsaturated $C_{1-7}$ acyclic aliphatic group optionally containing up to three heteroatoms independently selected from nitrogen, oxygen or sulfur; a $C_{5-7}$ cycloalkyl group; a phenyl group; a $C_{5-7}$ heterocyclic group; and wherein $R_A$ is selected from: hydrogen; a linear or branched, saturated or unsaturated $C_{1-7}$ aliphatic group optionally containing up to three heteroatoms independently selected from nitrogen, oxygen or sulfur; a $C_{5-7}$ cycloalkyl group; a phenyl group; a $C_{5-7}$ heterocyclic group;

and pharmaceutically acceptable salts thereof.

\* \* \* \* \*